United States Patent
Casad, Jr. et al.

(10) Patent No.: US 12,098,504 B2
(45) Date of Patent: Sep. 24, 2024

(54) METHODS AND DEVICES FOR PROCESSING LIGNOCELLULOSIC BIOMASS USING MECHANICAL PRETREATMENT TO ENHANCE FEEDSTOCK HYDRATION PROPERTIES

(71) Applicant: BIOFUEL TECHNOLOGY A/S, Egå (DK)

(72) Inventors: Robert C. Casad, Jr., Copenhagen (DK); Ib Johannsen, Risskov (DK)

(73) Assignee: TAB HOLDING APS, Egå (DK)

( * ) Notice: Subject to any disclaimer, the term of this patent is extended or adjusted under 35 U.S.C. 154(b) by 696 days.

(21) Appl. No.: 16/346,455

(22) PCT Filed: Nov. 2, 2017

(86) PCT No.: PCT/US2017/059646
§ 371 (c)(1),
(2) Date: Apr. 30, 2019

(87) PCT Pub. No.: WO2018/085487
PCT Pub. Date: May 11, 2018

(65) Prior Publication Data
US 2019/0309472 A1    Oct. 10, 2019

Related U.S. Application Data

(60) Provisional application No. 62/567,232, filed on Oct. 3, 2017, provisional application No. 62/416,438, filed on Nov. 2, 2016.

(51) Int. Cl.
*D21B 1/30*      (2006.01)
*C12P 19/02*     (2006.01)
(Continued)

(52) U.S. Cl.
CPC ............... *D21B 1/30* (2013.01); *C12P 19/02* (2013.01); *C12P 19/14* (2013.01); *D21C 1/02* (2013.01); *D21C 1/10* (2013.01); *C12P 2201/00* (2013.01)

(58) Field of Classification Search
CPC .............. D21C 1/02; D21C 1/04; D21C 1/10
See application file for complete search history.

(56) References Cited

U.S. PATENT DOCUMENTS 5,589,033 A * 12/1996 Tikka ................. D21C 3/26
                                                 162/84
8,057,639 B2   11/2011 Pschorn et al.
(Continued)

FOREIGN PATENT DOCUMENTS

DE   202007019668 U1 *  4/2015  ............ C12M 21/04
EP         177640 A2      4/1986
(Continued)

OTHER PUBLICATIONS

Theerarattananoon, et al., Effects of the pelleting conditions on chemical composition and sugar yield of corn stover, big bluestem, wheat straw, and sorghum stalk pellets, Bioprocess Biosyst Eng, 35, p. 615-623. (Year: 2011).*

(Continued)

*Primary Examiner* — Anthony Calandra
(74) *Attorney, Agent, or Firm* — Schmeiser, Olsen & Watts, LLP

(57) ABSTRACT

Hydrothermal pretreatment of mechanically compressed straw in unagitated reactors provides a simple and inexpensive solution to poor C5 monomer yields with autohydrolysis processes. Unlike raw straw, compressed straw pellets or briquettes can be pretreated on commercial scale using unagitated batch reactors or simplified unagitated continuous systems. The chemistry of hydrothermal pretreatment is thereby altered such that loss of C5 sugars to unwanted (Continued)

Differential hydration of raw wheat straw and briquetted wheat straw in room temperature water.

byproduct reactions is reduced. With compressed straw, water content can be introduced within the reactor while it is pressurized, which reduces energy costs and capital expense. Provided are methods of processing straw feedstocks using semi-continuous or continuous systems and a pretreatment reactor adapted to processes compressed straw with high throughput through a small reactor volume in which water content is added within the reactor under pressure.

17 Claims, 5 Drawing Sheets

(51) Int. Cl.
    *C12P 19/14*     (2006.01)
    *D21C 1/02*     (2006.01)
    *D21C 1/10*     (2006.01)

(56) References Cited

U.S. PATENT DOCUMENTS

| | | | |
|---|---|---|---|
| 2009/0308383 | A1 | 12/2009 | Shin et al. |
| 2010/0181034 | A1* | 7/2010 | Bradt ............ D21C 1/02 162/68 |
| 2010/0279361 | A1 | 11/2010 | South et al. |
| 2011/0110810 | A1 | 5/2011 | Burke |
| 2013/0029406 | A1 | 1/2013 | Dottori et al. |
| 2015/0147796 | A1 | 5/2015 | Bonde |

FOREIGN PATENT DOCUMENTS

| | | |
|---|---|---|
| WO | 2009108773 A2 | 9/2009 |
| WO | 2009125292 A2 | 10/2009 |
| WO | 2010113129 A2 | 10/2010 |
| WO | 2013152771 A1 | 10/2013 |
| WO | 2014019589 A1 | 2/2014 |
| WO | 2014129910 A1 | 8/2014 |
| WO | 2014183768 A1 | 11/2014 |
| WO | 2015014364 A1 | 2/2015 |
| WO | 2015169319 A1 | 11/2015 |
| WO | 2015172787 A1 | 11/2015 |
| WO | 2016004958 A1 | 1/2016 |

OTHER PUBLICATIONS

Saha et al., Dilute Acid pretreatment, enzymatic saccharification and fermentation of wheat straw to ethanol, 2011, Process Biochemistry, 40, p. 3693-3700. (Year: 2005).*
Tumuluru et al., A review of biomass densification systems to develop uniform feedstock commodities for bioenergy application, 2011, Biofuels, Bioprod. Bioref., %, p. 683-707. (Year: 2011).*
Smook, Handbook for Pulp and Paper Technologists, 1992, Angus Wilde Publications, 2nd edition, chapter 8. (Year: 1992).*
Stelte et al., Fuel pellets from biomass: The importance of the pelletizing pressure and its dependency on the processing conditions, 2011, Fuel, 90(11), p. 3285-3290. (Year: 2011).*
Rydholm, Pulping Processes, 1965, John Wiley and Sons, p. 663-665 and 681. (Year: 1965).*
English Machine translation of DE-202007019668-U1, 2022. (Year: 2022).*
Alakangas Eija, New European Pellets Standard—EN 14961-1, 2010 [downloaded online Feb. 14, 2024, VTT (Year: 2010).*
Kofman, Pieter, Preview of European standards for solid biofuels, 2010, downloaded online Feb. 14, 2024, VTT (Year: 2010).*
Hoekman, S. Kent, et al. "Process Development Unit (PDU) for Hydrothermal Carbonization (HTC) of Lignocellulosic Biomass", Waste and Biomass Valorization, vol. 5,(2014).
Sievers, D., et al., "Online residence time distribution measurement of thermochemical biomass pretreatment reactors," Chemical Engineering Science (2016) 140:330.

Steinman, W. and Eck, M. "Buffer storage for direct steam generation," Solar Energy (2006) 80:1277-1282.
Stelte, W. et al., "Fuel pellets from biomass: The importance of the pelleting pressure and its dependency on the processing conditions," Fuel (2011) 90:3285-3290.
Stelte, W. et al., "Recent developments in biomass pelletization—a review," BioResources (2012) 7(3): 4451-4490.
Sun, W. et al., "Operation optimization of steam accumulators as thermal energy storage and buffer units," Energies (2017) 10, 17; doi:10.3390/en10010017.
Tumuluru, J., et al., "Impact of process conditions on the density and durability of wheat, oat, canola, and barley straw briquettes," Bioenerg. Res. (2015) 8:388.
Wang. W., et al., "Effect of mechanical disruption on the effectiveness of three reactors used for dilute acid pretreatment of corn stover. Part 1 : chemical and physical substrate analysis," Biotechnology for Biofuels (2014) 7:57.
Yao, S. et al. "Efficient extraction of bagasse hemicelluloses and characterization of solid remainder," Bioresource Technology (2015)185:2.
Zhang, Q. et al. (2015) "Effects of ultrasonic vibration-assisted pelleting on chemical composition and sugar yield of corn stover and sorghum stalk," Renewable Energy 76:160-166.
Zhang, J. et al., "Reactors for high solid loading pretreatment of lignocellulosic biomass," Adv. Biochem. Eng. Biotechnol. (2016), 152:75-90.
Zhang, Q. et al. (2017) "Investigation on characteristics of corn stover and sorghum stalk processed by ultrasonic vibration-assisted pelleting," Renewable Energy 101 :1075-1 086].
Kling, S. et al. "Enhancement of enzymatic hydrolysis of sugar cane bagasse by steam explosion pretreatment," Biotechnology and Bioengineering (1987) 29:1035.
Kumar, R. et al. "Carbohydrate-derived pseudo-lignin can retard cellulose bioconversion," Biotechnology and Bioengineering (2013) 11 0(3) :737.
Lara-Vazquez, A. et al., "Particle size and hydration medium effects on hydration properties and sugar release of wheat straw fibers," Biomass and Bioenergy (2014) 68:67.
Li, H. et al. "pH pre-corrected liquid hot water pretreatment on corn stover with high hemicellulose recovery and low Inhibitors formation," Bioresource Technology (2014) 153:92.
Lischeske, J. et al., "Assessing pretreatment reactor scaling through empirical analysis," Biotechnology for Biofuels (2016) 9:213.
Mani, S., et al., "Effects of compressive force, particle size and moisture content on mechanical properties of biomass pellets from grasses," Biomass and Bioenergy (2006) 30:648-654.
Adapa, P. et al., "Compaction characteristics of barley, canola, oat and wheat straw," Biosystems Engineering (2009) 104:335-344.
Allen, S. "A comparison between hot liquid water and steam fractionation of corn fiber," Ind. Eng. Chem. Res. ( 2001 ) 40 :2934.
Alvira, P. et al. "Effect of endoxylanase and alpha-L-arabinofuranosidase supplementation on the enzymatic hydrolysis of steam exploded wheat straw," Bioresource Technology (2011) 102:4552-4558.
Ballesteros, I. et al. "Ethanol production from steam-explosion pretreated wheat straw," Applied Biochemistry and Biotechnology (2006) 129-132:4996-5008.
Bossel, U. "Production and marketing of briquettised and pelletised solid biomass fuels," Bioenergy 84, vol. 1, 1984.
Bychkov, A. et al. "Ultrastructural changes of cell walls under intense mechanical treatment of selective plant raw material," Biomass and Bioenergy (2012) 47:260.
Ciesielski, P et al., "Effect of mechanical disruption on the effectiveness of three reactors used for dilute acid pretreatment of corn stover Part 2: morphological and substrate analysis," Biotechnology for Biofuels (2014) 7:47.
Dupont, C. et al., "Heat capacity measurements of various biomass types and pyrolysis residues," Fuel (2014) 114:644-651.
Ghosh, A. et al. "Enhancing dropwise condensation through bioinspired wettability patterning," Langmuir (2014) 30:13103.
Ibbett, R. et al. "The mechanisms of hydrothermal deconstruction of lignocellulose: New insights from thermal-analytical and complementary studies," Bioresource Technology (2011) 102:9272.

(56) References Cited

OTHER PUBLICATIONS

Ibbett, R. et al. "The kinetics of inhibitor production resulting from hydrothermal deconstruction of wheat straw studied using a pressurised microwave reactor," Biotechnology for Biofuels (2014) 7:45.

Jurado, M. et al. "Laccase detoxification of steam-exploded wheat straw for second generation bioethanol," Bioresource Technology (2009) 100:6378-6384.

Moset. V., et al., "Optimization of methane yield by using straw briquettes—influence of additives and mold size," Industrial Crops and Products (2015) 7 4:925.

Rasmussen, H. et al., "Formation of degradation compounds from lignocellulosic biomass in the biorefinery: sugar reaction mechanisms," Carbohydrate Research (2014) 385:45].

Rasmussen, H. et al., "New degradation compounds from lignocellulosic biomass pretreatment: routes for formation of potent oligophenolic enzyme inhibitors," Green Chemistry (2016) DOI: 10.1 039/c6gc01809b.

Rijal, B. et al., "Combined effect of pelleting and pretreatment on enzymatic hydrolysis of switchgrass," Bioresource Technology (2012) 116:36-41.

Sannigrahi, P. et al. "Pseudo-lignin and pretreatment chemistry," Energy & Environmental Science (2011) 4:1306.

Chen, J. et al., "Screw extruded steam explosion: A promising pretreatment to enhance enzymatic hydrolysis, " Biosource Technology (2014) 161:230.

Choi, C., et al., "The influence of screw configuration on the pretreatment performance of a continuous twin screw driven reactor." Bioresource Technology (2013) 132:49.

Grover, P. and Mishara, S. Biomass briquetting: Technology and practice in Regional Wood Energy Development Program in Asia, Tech report GCP/RAS/154/NET. Food and Agriculture Organization of the United Nations, Bangkok, Thailand (1996).

He, Y., et al., "Helically agitated mixing in dry dilute acid pretreatment enhance the bioconversion of corn stover into ethanol," Biotechnology for Biofuels (2014) 7:1.

Li, Y. et a. "Responses of biomass briquetting and pelleting to water-involved pretreatments and subsequent enzymatic hydrolysis," Bioresource Technology (2014) 151:54-62.

Petersen, M. et al. "Optimization of hydrothermal pretreatment of wheat straw for production of bioethanol at low water consumption without addition of chemicals," Biomass and Bioenergy (2009) 33:834.

Zheng, J., et al. "The effects of screw elements on enzymatic digestibility of corncobs after pretreatment in a twin-screw extruder," Biomass and Bioenergy (2015) 74:224-232.

* cited by examiner

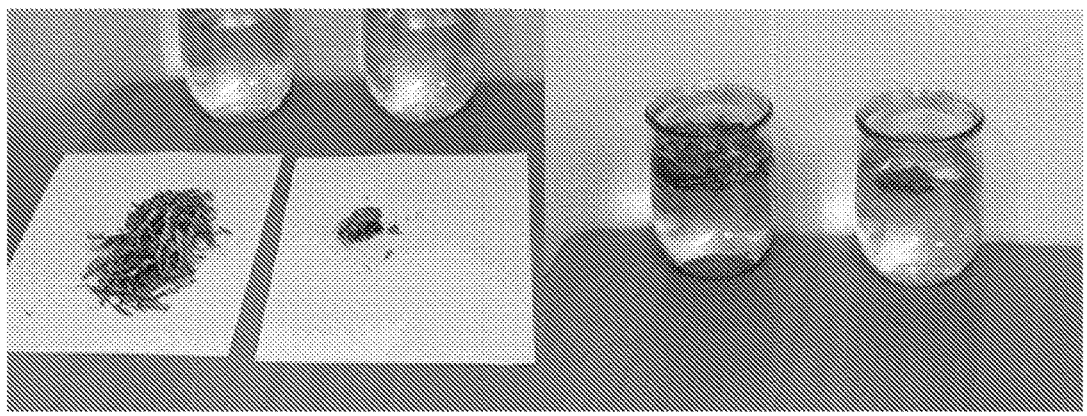
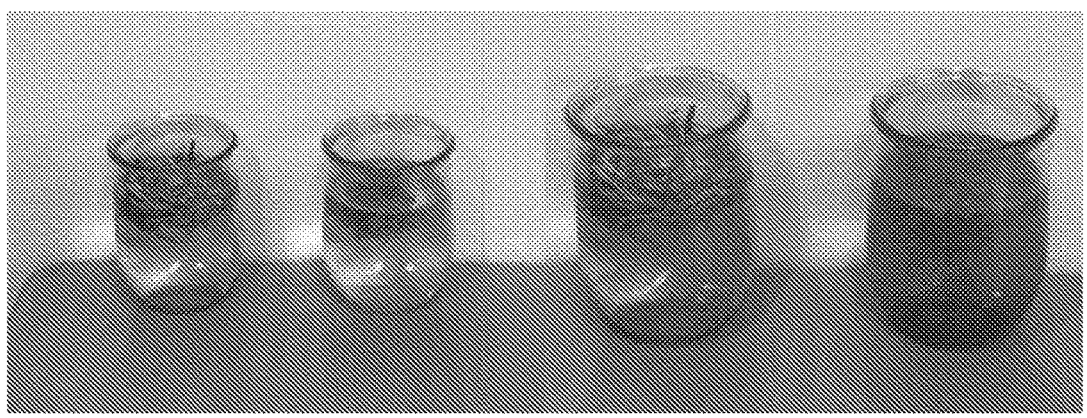
Figure 1. Differential hydration of raw wheat straw and briquetted wheat straw in room temperature water.

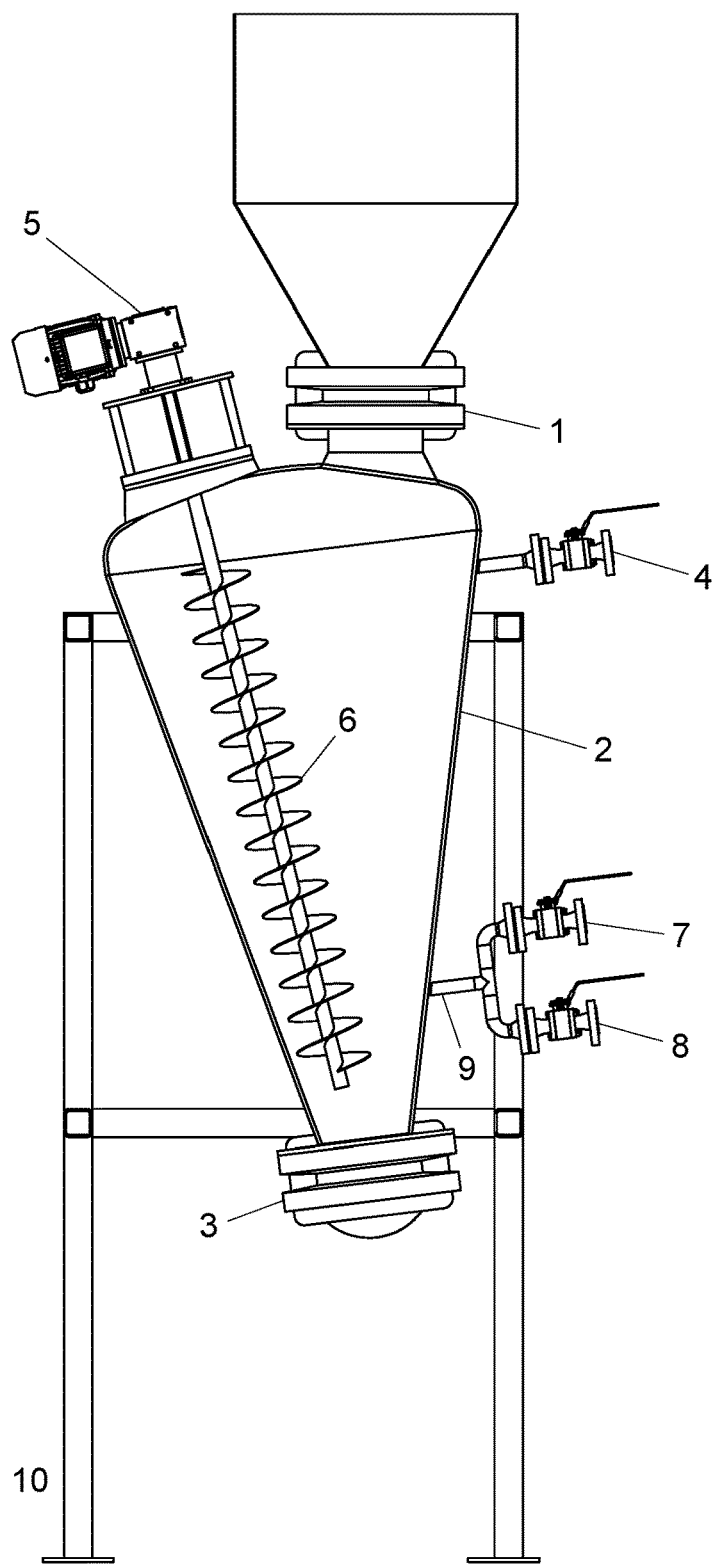
Figure 2. Hydrothermal pretreatment reactor

Figure 3. Visual appearance of raw wheat straw after unagitated steam pretreatment to log Ro 3.76.

Figure 4. Visual appearance of briquetted wheat straw after unagitated steam pretreatment to log Ro 3.76.

Figure 5. Differentially pretreated component tissues from raw straw subjected to unagitated steam pretreatment to log Ro 3.76.

METHODS AND DEVICES FOR PROCESSING LIGNOCELLULOSIC BIOMASS USING MECHANICAL PRETREATMENT TO ENHANCE FEEDSTOCK HYDRATION PROPERTIES

This application claims priority to U.S. provisional patent applications 62/416,438 filed Nov. 2, 2016, and 62/567,232 filed Oct. 3, 2017, which are hereby incorporated by reference in entirety. This invention was made in part with support of the Danish State Innovations Fund under Jnr. 101-2014-1.

FIELD

The invention relates generally to methods and devices for processing lignocellulosic biomass and specifically to methods and devices utilizing hydrothermal pretreatment of feedstocks that have been previously subjected to mechanical compression.

BACKGROUND

Lignocellulosic biomass processing for production of fuels, chemical precursors and other products is widely expected to play a central role in a prospective sustainable economy.

The total yield of both C5 and C6 sugars is a central consideration in commercialization of lignocellulosic biomass processing. In the case of ethanol production, and also production of lactate or other fermentation products, it can be advantageous to combine both C5 and C6 sugar process streams into one sugar solution. Genetically modified fermentive organisms are now available which can efficiently consume both C5 and C6 sugars in ethanol production.

Because of limitations of its physical structure, lignocellulosic biomass cannot be effectively converted to fermentable sugars by methods relying on enzymatic hydrolysis without some pretreatment process. Pretreatment generally seeks to optimize enzyme consumption. Enzyme consumption is a central consideration in commercialization of biomass processing, which teeters on the verge of "economic profitability" in the context of "global market economies" as these are currently defined. Notwithstanding dramatic improvements in recent years, the high cost of commercially available enzyme preparations remains one of the highest operating costs in biomass conversion.

A wide variety of different pretreatment schemes have been reported, each offering different advantages and disadvantages. From an environmental and "renewability" perspective, hydrothermal pretreatments are especially attractive. These utilize pressurized steam/liquid hot water at temperatures on the order of 160-230° C. to gently melt hydrophobic lignin that is intricately associated with cellulose strands, to solubilize some of the hemicellulose, rich in C5 sugars, and to disrupt cellulose strands so as to improve accessibility to productive enzyme binding.

In the case of hydrothermal pretreatment schemes, a first stage mechanical pretreatment can be advantageous whereby the feedstock is compressed, as in production of biomass pellets or briquettes. Mechanical compression reduces biomass transportation and storage costs and, in some contexts, results in higher eventual sugar yield after hydrothermal pretreatment and enzymatic hydrolysis. The increased sugar yields with compressed feedstocks have been attributed to high temperatures achieved in compression die-molds during processing and to particle size reduction, which is typically a feature of mechanical compression schemes. See e.g. Zhang et al. 2017; Zhang et al. 2015; Rijal et al. 2012.

We have discovered that, surprisingly, at least in the case of straw feedstocks, mechanical compression also alters hydration properties in a manner that can be exploited to great advantage in hydrothermal pretreatments. Unlike raw straw, compressed straw directly absorbs steam condensate in typical hydrothermal pretreatment conditions. This has two commercially significant consequences: First, compressed straw "cooks" evenly in pressurized steam, without any requirement for agitation. It is therefore possible to pretreat compressed straw in large, unagitated batch reactors, which are very inexpensive compared with typical continuous pretreatment systems. In contrast, raw straw typically exhibits heterogeneous "cooking" and is typically agitated in continuous systems by action of a transport screw or by specially designed steam systems and/or by explosive release to atmospheric pressure. Second, the chemistry of hydrothermal pretreatment is altered. In an unagitated semi-continuous or continuous pretreatment with compressed straw, loss of C5 sugars to unwanted byproduct reactions can be greatly reduced. This also reduces the incidence of compounds which inhibit cellulase enzymes, yeast and biomethane production.

An additional advantage of the altered hydration properties of compressed straw is a tendency for very rapid swelling in water, compared with raw straw. As a consequence, with compressed straw, unlike raw straw, it is possible to add water content under pressure, at reaction temperature. Substantial throughput can be achieved using inexpensive batch reactors in semi-continuous, sequential batch mode, either using pre-wetted feedstocks or dry feedstocks to which water content is added at reaction temperature. The pretreated material can be unloaded from the reactor avoiding agitation associated with explosive release through application of mild over-pressure, ideally on the order of 3-4 bar alone or in combination with the introduction of water content, which will ultimately be added in any case to dilute dry matter content of the pretreated whole slurry. The underlying technical effects can also be exploited in greatly simplified continuous systems.

The use of dry feedstocks to which water content is added at reaction temperature has additional advantages. A simple pressure reactor can be filled very quickly with dry straw pellets using only a small, inexpensive valve. Heated water can then be added under pressure both to achieve appropriate water content and also to affect hydrothermal pretreatment. This both simplifies the technical requirements for the boiler system and also reduces the overall energy cost of pretreatment. Effective hydrothermal pretreatment of a biomass feedstock requires considerable water content—typically at least 50% by weight. Water is both reactant and catalyst in hemicellulose hydrolysis, which is the primary desired chemical reaction. Water content is also required to "safely" solubilize sugars released during hemicellulose hydrolysis while minimizing destructive byproduct reactions. When steam is used to heat water content of the biomass, the mass of steam condensate produced during heating is unnecessary water wastefully heated to reaction temperature. The magnitude of this unnecessary heating can be as much as 35% of total pretreatment energy cost. While much of this heat can be recovered for use in other biorefinery processes, the reduction in unnecessary heating is advantageous in any case, minimizing losses and reducing boiler capacity requirements.

Previously it was widely believed that continuous pretreatment is critical for an efficient commercial-scale lignocellulosic biomass refinery. While continuous systems are inherently more energy efficient than semi-continuous ones, this increased efficiency is less significant in small scale plants with capacity on the order of 5-8 tons per hour compared with large scale plants having capacity 50-100 tons per hour. Continuous pretreatment systems for raw straw are typically complex and expensive, requiring heavy moving parts and screw plug feeders or elaborate sluice systems. In part as a consequence of the capital expense of continuous pretreatment systems, biorefineries have previously only proved commercially feasible on very large scale. It can be particularly attractive for smaller scale biorefinery projects or even for biogas plants in countries that subsidize biogas production to conduct hydrothermal pretreatment of compressed straw feedstocks with inexpensive semi-continuous systems that avoid agitation and associated degradation of C5 sugars.

Hydrothermal pretreatment of compressed straw in unagitated reactors provides a simple and inexpensive solution to poor C5 monomer yields with autohydrolysis processes. It is well known in the art, and has been widely discussed, that hydrothermal pretreatment must be optimized between conflicting purposes. On the one hand, pretreatment should ideally preserve hemicellulose sugar content to maximize ultimate yields of monomeric hemicellulose-derived sugars. Yet pretreatment should also sufficiently expose and precondition cellulose chains to susceptibility of enzymatic hydrolysis so as to minimize enzyme consumption. Higher temperatures and residence times are required to properly condition cellulose fibers for efficient enzymatic hydrolysis to monomeric 6-carbon glucose. Yet, as temperatures and reactor residence times are increased, a greater proportion of C5 sugars derived from hemicellulose is irretrievably lost due to chemical transformation to other substances, including furfural and products of condensation reactions. A related problem is that many soluble byproducts of C5 degradation during hydrothermal pretreatment are known to inhibit cellulase enzyme catalysis. See e.g. Rasmussen et al. (2016); and see Rasmussen et al. (2014).

A variety of different hydrothermal pretreatment strategies have been reported for maximizing sugar yields and for minimizing cellulase catalysis inhibitors. In some cases, exogenous acids or bases are added to catalyse hemicellulose degradation (acid; pH<3.5) or lignin solubilisation (base; pH>9.0). In other cases, hydrothermal pretreatment is conducted as an "auothydrolysis" process without added acid or base, under essentially neutral conditions (pH 5.0-8.0). Acid catalysed hydrothermal pretreatments, known as "dilute acid" or "acid impregnation" processes, typically provide high C5 sugar yields, since comparable hemicellulose solubilisation occurs at lower temperatures in the presence of acid catalyst. Autohydrolysis processes typically provide much lower yields of soluble C5 sugars than can be achieved with acid catalysts. Yet notwithstanding lower C5 yields, autohydrolysis offers competitive advantages over dilute acid pretreatments on commercial scale. Autohydrolysis processes are inherently simple and also avoid well known disadvantages of dilute acid. The requirement for sulphuric acid diverges from a philosophical orientation favouring "green" processing, introduces a substantial operating cost for acid as process input, deleteriously alters chemical properties of lignin recovered from the process, and further creates a need for elaborate waste water treatment systems and for expensive anti-corrosive equipment.

Poor C5 monomer yields with autohydrolysis has driven commercial providers of lignocellulosic biomass processing technology to pursue other approaches. Some "two-stage" pretreatment systems, designed to minimize C5 degradation, have been reported in which some C5-rich liquid fraction is removed by solid/liquid separation after a lower temperature "first stage" pretreatment, followed by a subsequent, higher temperature "second stage" pretreatment of the solid fraction. See WO2010/113129; US2010/0279361; WO 2009/108773; US2009/0308383; U.S. Pat. No. 8,057,639; US20130029406. The loss of C5 sugars in autohydolysis pretreatments of the prior art has also been associated with a significant accumulation of soluble byproducts which are toxic to cellulase enzyme preparations and which required solid/liquid separation steps to remedy. See WO2014/019589 and WO2015/014364 (each of which is hereby expressly incorporated by reference in entirety).

The problems of high C5 degradation with autohydrolysis processes and resulting accumulation of soluble inhibitors which were solved in the prior art by elaborate two-stage pretreatments or solid/liquid separation steps can alternatively and advantageously be solved by simple, inexpensive unagitated pretreatment of previously compressed feedstock.

SUMMARY

Hydrothermal pretreatment of mechanically compressed straw in unagitated reactors provides a solution to poor C5 monomer yields with autohydrolysis processes that is simple and inexpensive compared with prior art solutions. Unlike raw straw, compressed straw directly absorbs steam condensate in typical hydrothermal pretreatment conditions. This ensures that compressed straw "cooks" evenly in pressurized steam, without any requirement for agitation, and permits pretreatment using simple, inexpensive, unagitated batch reactors. Compressed straw absorbs water rapidly such that pretreatment can be conducted using straw pellets or briquettes introduced into such reactors dry with water content added at reaction temperature, under pressure. These technical effects can also be exploited in simplified continuous systems. In unagitated pretreatment with compressed straw, the chemistry of hydrothermal pretreatment is altered such that loss of C5 sugars to unwanted byproduct reactions can be greatly reduced.

BRIEF DESCRIPTION OF THE DRAWINGS

FIG. 1 shows differential hydration of raw wheat straw and briquetted wheat straw in tap water at room temperature.

FIG. 2 shows a suitable unagitated hydrothermal pretreatment reactor for lignocellulosic biomass processing.

FIG. 3 shows visual appearance of raw wheat straw after unagitated steam pretreatment to log Ro 3.76.

FIG. 4 shows visual appearance of briquetted wheat straw after unagitated steam pretreatment to log Ro 3.76.

FIG. 5 shows differentially pretreated component tissues from raw straw subjected to unagitated steam pretreatment to log Ro 3.76.

DESCRIPTION OF EMBODIMENTS

In some embodiments, the invention provides a method of processing lignocellulosic biomass comprising the steps of:
(i) providing wheat or other straw,
(ii) subjecting said straw to hydrothermal pretreatment at a water content during pretreatment of at least 40% for a residence time of between 1 and 120 minutes at a temperature between 160° and 220° C. in batch-mode in a pressure reactor equipped with at least one inlet valve and at least one outlet valve in such manner that agitation of the feedstock during pretreatment is avoided either by mechanical means or by explosive release of pretreated material to lower pressure, (iii) removing pretreated straw from the pressure reactor, and (iv) sequentially repeating the batch-mode preteatment so as to maintain a semi-continuous process.

In some embodiments, the invention provides a method of processing lignocellulosic biomass comprising the steps of:
(i) providing wheat or other straw that has been mechanically compressed to specific density at least 500 kg/m3 and that exhibits a time to swelling factor of less than 12.0 or a rapid hydration swelling factor of at least 7.0 or both, and
(ii) subjecting said compressed straw to continuous hydrothermal pretreatment in a pressure reactor for a residence time of between 1 and 120 minutes at a temperature between 160° and 220° C. in such manner that agitation of the feedstock during pretreatment is avoided either by mechanical means or by explosive release of pretreated material to lower pressure,
wherein water content during pretreatment of at least 40% is achieved primarily by adding water to the straw inside the reactor when it is pressurized, and
wherein the straw is compressed with an applied pressure less than 500 bar by ring die or flat die pelleting or by piston compression briquetting.

As used herein, the following terms have the following meanings:

"Hydrothermal pretreatment" refers to the the use of water either as hot liquid, pressurized steam, or both to "cook" biomass at temperatures within the range 160-230° C.

"Water content during pretreatment" refers to the weight percentage water content of the feedstock during pretreatment immediately before de-pressurization including initial water content of the feedstock at the time of exposure to mass and heat transfer from added steam or hot water plus any steam condensate absorbed by the biomass and any other water content directly added during pretreatment. Water content is "achieved primarily by adding water to the straw inside the reactor when it is pressurized" to the extent that the predominant proportion of total water content is added under pressure inside the reactor.

"For a residence time of between 1 and 120 minutes at a temperature between 160° and 220° C." refers to the amount of time the feedstock being pretreated is within the pressure reactor while the temperature within the reactor is within the range 160° to 220° C.

"The pH at which the feedstock is pretreated" is the initial pH of water content in the feedstock at the time of exposure to mass and heat transfer from added steam or hot water.

"Batch-mode" refers to a hydrothermal pretreatment process in which a quantity of biomass is used to fill a reactor in which the biomass is pretreated and then removed without additional loading and unloading of the reactor during the pretreatment of said quantity of biomass. "Continuous" mode refers to a hydrothermal pretreatment in which quantities of biomass are continuously fed into and removed from a pressurized reactor in a steady-state process. "Semi-continuous" mode refers to a hydrothermal pretreatment process in which a "batch-mode" process is repeated sequentially.

"Agitation of the feedstock during pretreatment" refers to processes whereby the biomass and/or accumulated liquid is caused to experience mixing, either through action of a transport screw or other transport mechanism, or through introduction of pressurized steam in a manner intended to cause mixing, or by mechanical manipulation in a manner intended to cause mixing, or through explosive release of pretreated material from reactor pressure to atmospheric pressure or any lower pressure. Agitation is "during pretreatment" to the extent that it occurs within the temperature range 160° to 220° C. It will be readily understood that some agitation prior to reaching reaction temperature and/or after de-pressurization can be advantageous. "Agitation during pretreatment" is "avoided" to the extent that incidental agitation is intentionally minimized, for example, where transport means or other sources of agitation useful in loading and/or unloading a reactor are predominantly turned off during residence time within the temperature range 160° to 220° C. An "unagitated" reactor or an "unagitated" mode of operation is a reactor or a mode of operation that "avoids" "agitation of the feedstock during pretreatment."

"Explosive release" refers to release of biomass from the pressure reactor in which the biomass experiences a pressure drop of >4 bar on exiting the reactor. Use of over-pressure to purge biomass from a reactor is not "explosive release" where the biomass does not experience a pressure drop>4 bar on exiting the reactor. "Removing pretreated straw from the pressure reactor using non-explosive over-pressure" refers to use of over-pressure of not more than 4 bar to purge pretreated biomass from the reactor either by itself or in combination with other treatments such as washing with water content. It will be readily understood that the pressure reactor may be one component of a system in which pretreated biomass is removed from one component and transported to another.

"Density" as applied to compressed biomass refers to average specific density determined as (mass/volume) of single individual pellets, briquettes or other small samples expressed in theoretical units of kg/m3. The expression in terms of kg/m3 is not intended to imply a bulk density. The units kg/m3 for density can alternatively be expressed as g/liter. "Compressed to a density" refers to the condition of the feedstock after it has been unloaded from a compression system.

"Applied pressure" refers to the pressure applied by the piston directly as compressed biomass is pushed forward through the die mold in a piston compression system; or to the pressure applied by rollers acting on a surface perpendicular to press channels so as to initially compress biomass and then force it into press channels against a friction pressure built up between the press channels and biomass within the press channels in either a ring die or flat die pelleting system. "Pressure" refers to the average force per unit area of contact applied perpendicular to the "plane" of the biomass pieces during compression.

"Fiber structure is substantially preserved" refers to the qualities of feedstock after some mechanical treatment characterised in that, in optical microscopic resolution at 50 um scale, individual cells of fibers are substantially conjoined in large groups having size much larger than 50 um, with limited evidence of disruption (where individual cells are separated from each other) or of breakage of groups of conjoined cells into smaller groups having size on the order of 50 um or less.

"Structurutal wall thickness" refers to the thickness of the biomass wall which circumscribes the lumen of the straw. Viewing straw as (on average) effectively a hollow "cylinder" of biomass, the thickness of the walls of the "cylinder" is "structural wall thickness." It will be readily understood by one skilled in the art that straw has different anatomical parts, and that the degree of "compression" of "structural wall thickness" can be defined only as a crude average with wide variability.

"Time to swelling factor" refers to a measurement determined as follows: A tested feedstock having specific density at least 500 kg/m3 is first dried by warming at 100° C. for 60 minutes. The apparent volume occupied by 60 g of the dried feedstock is noted. "Apparent volume" of dry samples refers to the volume occupied by feedstock having on average pieces<2 cm in longest dimension, or of wetted samples after straining when placed in one or more 250 ml graduated cylinder having internal diameter of 3.4-3.5 cm in such manner so as to minimize void space but without active compression. The feedstock sample is then placed in 1000 g water at room temperature in a cylindrical flask and allowed to sit without agitation. The swelled feedstock is then strained through a sieve by gravity and the apparent volume occupied by the wetted sample determined. The "time to swelling factor" is the number of minutes required for apparent volume occupied by the feedstock to increase by a factor of 3.0 in room temperature tap water as described with values expressed as the mean of N=4 determinations. A sample calculation—60 g wheat straw that had been pelleted using a ring die pellet press to specific density 1000 kg/m3 were tested as described. An apparent volume of 104 ml dry sample swelled to an apparent volume of 420 ml in 8.9 minutes; 102 ml dry swelled to 396 ml in 7.5 minutes; 107 ml swelled to 330 ml in 7.0 minutes; 108 ml swelled to 325 ml in 6.5 minutes. The calculated time to swelling factor for pelleted wheat straw in this case was the mean of <8.9, <7.5, <7.0, <6.5 or <7.5.

"Rapid hydration swelling factor" (RHSF) refers to a measurement determined as follows: A tested feedstock is first dried by warming at 110° C. for 60 minutes. 4 g of the dried feedstock is mixed with 125 g of water at room temperature in a glass jar that is covered with a sieve having average aperture area about 6 mm^2. The weight of the glass jar with sieve cover is determined before the test. The feedstock with water at 20° C. is allowed to sit for 30 minutes in the glass jar with sieve cover. After 30 minutes the glass jar is inverted for a period of 1 minute so that free water passes by gravity through the sieve cover while wetted feedstock is retained by the sieve cover. Total wet weight of the wetted feedstock is then determined. The rapid hydration swelling factor is the ratio of wet weight/dry weight of the tested feedstock sample where wetting is determine as described, with values expressed as the mean of N=4 independent determinations. A sample calculation—raw wheat straw was tested as described. An initial dry weight of 4.0 g became a wetted weight as described of 17.8+/−0.2 g (N=4). The calculated rapid hydration swelling factor for raw straw in this case was (17.8)/(4.0)=4.45. Wheat straw that had been subjected to reciprocating piston compression with an applied piston pressure of about 350 bar to a density of 750 kg/m3 was tested. An initial dry weight of 4.0 g became a wetted weight as described of 38.7+/−0.1 g (N=4). The calculated rapid hydration swelling factor for briquetted wheat straw in this case was (38.7)/(4.0)=9.68.

"Water content at which feedstocks are subjected to mechanical compression" is the water content of the feedstock after any particle size reduction but prior to compression.

"Packing density in the occupied reactor volume" refers to the density in kg dry matter (DM)/liter reactor volume at which the feedstock is loaded into that portion of the pressure reactor which it occupies during pretreatment. It will be readily understood that the feedstock may be loaded in such manner as to avoid contact with the reactor walls, leaving some void space, and that the reactor may be intentionally left partially empty to facilitate removal of pretreated biomass by non-explosive over-pressure such that the "occupied reactor volume" is less than the total internal volume. "Pressure reactor filling level" refers to the percentage of total internal volume of the pressure reactor which is "occupied reactor volume" for purposes of calculating "packing density in the occupied reactor volume."

"Central axis" refers to the theoretical axis of rotation of a pressure tank or stirring auger when rotated.

Methods of the invention are particularly advantageously applied to straw including wheat, barley, rice, oat, rye, canola, rape, rice and corn straw (stover). However, other suitable lignocellulosic biomass feedstock may also be used including grasses such as switchgrass, bermuda grass, miscanthus and reed canarygrass.

In some embodiments, straw feedstock has been subject to mechanical compression prior to hydrothermal pretreatment. It has been widely suggested that compression of feedstocks "in the field" will improve logistics of biomass supply to centralized biorefineries because volume reduction reduces transportation costs and because high temperatures achieved within compression dies (typically over 100° C.) sterilize the feedstock and thereby prevent loss of fermentable sugars to bacterial rot. To obtain these advantages, about 5-fold volume compression relative to bales is adequate. With straws, this is typically achieved where specific density is at least 500 kg/m3. In some embodiments, straw feedstock is compressed to a specific density of at least 500 kg/m3, or at least 600 kg/m3, or at least 700 kg/m3, or between 500-850 kg/m3, or between 500-999 kg/m3, or between 750-999 kg/m3, or between 500-1250 kg/m3, or less than 1000 kg/m3, or less than 1100 kg/m3. As will be readily understood by one skilled in the art, mechanical compression may be conducted at one location that is geographically remote (>5 km distance) from the location of hydrothermal pretreatment. For example, straw feedstocks may be pelleted "in the field" using newly developed technology which simultaneously harvests and pelletizes. Accordingly, in some embodiments methods of the method invention may be construed as simply conducting unagitated hydrothermal pretreatment of feedstock that was previously subject to mechanical compression.

The differential hydration properties of pelleted or briquetted straw are readily apparent to the naked eye. FIG. 1 shows the behavior in tap water at room temperature of 6 g each of ordinary raw wheat straw and wheat straw briquetted by piston compression to specific density 750 kg/m3. The nominal apparent volume of each is shown at 0, 10 and 30 minutes. As shown, the briquetted straw initially occupies about ⅙ the apparent volume of raw straw. Within 10 minutes in an excess of water, the briquetted straw has expanded to about ½ the volume of raw straw, which remains unchanged. Pelletized straw exhibits similar rapid hydration.

The exact physical mechanisms for the enhanced rapid water absorption by pelleted or briquetted straw is not yet understood. Densification of the feedstock alone, in and of itself, is not sufficient to produce this effect. Without wishing to be bound by theory, we speculate that enhanced rapid water absorption occurs to the extent that compression alters straw fiber structure such that permeation barriers which contribute to water transport properties of the native fiber are destroyed while basic fiber structure is substantially preserved. As a consequence, intrinsic capillarity of compressed straw fiber is enhanced relative to that of raw straw native fiber.

In some embodiments, straw is compressed into either pellets or briquettes. The terms "pellets" and "briquettes" primarily refer to similar material having different dimensions, pellets being smaller and briquettes being larger, for example, as defined in European standards for biomass solid fuels EN 14961-1 and EN 14961-3. The underlying processes for production of pellets and briquettes are closely related. Typically briquettes are made using direct piston compression where the piston acts in line with the briquetting die. Pellets are typically made using a system of rollers which roll across a surface that is perpendicular to the press channels through which compressed biomass is forced. Suitable compression of straw feedstocks can be obtained using either a ring die or flat die "pelletizing" system, either a mechanical or hydraulic piston compression system, or any compression system known in the art used in such manner so as to produce compressed feedstock having either a time to swelling factor of less than 12.0 or a rapid hydration swelling factor of at least 7.0 or both. Enhanced rapid hydration swelling is already apparent in wheat straw briquetted or pelleted to a specific density at least 500 kg/m3.

One skilled in the art can readily determine, without undue experimentation, appropriate conditions for mechanical compression that will impart a time to swelling factor of less than 12.0 or a rapid hydration swelling factor of at least 7.0. In some embodiments, compression is achieved in such manner that fiber structure of the feedstock is substantially preserved. In some embodiments, structural wall thickness of straw internodes is compressed on average during mechanical compression by a factor of at least 1.5× relative to raw straw, or at least 2.0×, or at least 2.1×, or at least 2.2×, or at least 2.3×, or at least 2.4×, or at least 2.5×, or at least 3.0×, or at least 3.5×, or at least 4.0×, or between 4.0-4.9×, but less than 5.0×, or between 1.5 and 2.9×, but less than 3.0×, or less than 4.0×. In some embodiments, mechanical compression is applied after some initial particle size reduction. This can be advantageously achieved in such manner that fiber structure is substantially preserved. As noted by Lara-Vazquez et al. (2014), grinding to very fine particle sizes collapses the fiber matrix and reduces the "water retention capacity" of the feedstock. Cutting and/or milling can readily be achieved in such manner that fiber structure of the feedstock is substantially preserved. In some embodiments, cutting and/or milling can be provided by first shredding the feedstock followed by processing using a hammer mill. Technology for shredders and hammer mills are well known in the art. In hammer milling, hammers mounted on a rotor disc force biomass through a screen and thereby affect particle size reduction while substantially preserving fiber structure of the feedstock. In contrast, ball milling is not generally suitable since this destroys fiber structures. See e.g. Bychokov et al. (2012). In some embodiments, initial particle size reduction prior to compression achieves pieces having lengths between 2-50 mm. One skilled in the art will readily imagine other means, including means well known in the art, for achieving pieces having lengths between 2-50 mm in which fiber structure is substantially preserved. In some embodiments, after particle size reduction the form of the feedstock is in pieces between 2-10 mm, or between 10-50 mm, or between 5-25 mm, or between 15-40 mm. It will be readily understood by one skilled in the art that pieces will have a distribution of sizes and that some small quantities of pieces will fall outside the claimed range. The range of lengths as used here refers to a distribution of particle sizes that accounts for 95% of the total mass of particles. In some embodiments, biomass feedstocks are subjected to mechanical compression at moisture content between 10-15% w/w, or between 5-15%, or not more than 5%, or not more than 10%, or not more than 15%, or not more than 20%. In some embodiments, time to swelling factor of the feedstock after compression is less than 12.0, or less than 11.0, or less than 10.0, or less than 9.5, or less than 9.0, or less than 8.0, or less than 7.0, or less than 6.0, or less than 5.0, or less than 4.0, or less than 3.0. In some embodiments, rapid hydration swelling factor is increased by mechanical compression to levels at least 6.0, or at least 7.0, or at least 7.5, or at least 8.0, or at least 8.5, or at least 9.0, or at least 9.5, or at least 10.0, or between 7.0 and 12.0, or between 7.5 and 11.5, or between 6.0 and 12.0.

Mechanical systems typically used for pelletting compared with briquetting differ somewhat in their technical principles. Pellet mills affect compression by application of rollers that roll across a flat or curved surface which is oriented more-or-less perpendicular to cylindrical press channels. Rollers initially compress biomass as well as force it into and through the press channels. The major applied force which acts upon the biomass feedstock to affect compression is the so-called "pelletizing pressure," which is primarily friction pressure that builds up between the press channels and the biomass. The actual pressure applied by rollers is usually adjusted to be of the same magnitude as the "pelletizing pressure," i.e. just enough to force biomass out of the press channels. With straw feedstocks, this "pelletizing pressure" is typically at most about 60 bar. See Stelte et al. (2012) and see Stelte et al. (2011). Many studies report much higher applied pressures from 316-1389 bar in formation of straw pellets. See e.g. Adapa et al. (2009); and see Mani et al. (2006). However, these studies are based on in-line piston compression in a closed cylinder and represent an overestimate of the applied pressure in an actual pellet mill. See Stelte et al. (2011) The applied pressure required in piston compression briquetting systems in the case of straw feedstocks is typically higher than that required in pelleting systems. These systems directly apply pressure in line with the briquetting die, which is typically not cylindrical but rather tapered so as to increase resistance to piston pressure. As a consequence, some precautions should be taken to avoid applying too much force when using piston compression to practice methods of the invention. In exploring structural changes in fibers which account for increased rapid hydration swelling, we determined RHSF values for raw wheat straw that was subjected either to compression by a single piston within a closed cylinder with an applied pressure of >1500 bar or to compression with >1500 bar pressure combined with explosive release to atmospheric pressure from the compression chamber through a small orifice. In these experiments, orifice-exploded compressed raw straw exhibited an RHSF value of 7.25 on average, which is close to the level 9.68 observed with straw briquetted to a density of 750 kg/m3 using an applied pressure of about 350 bar. In contrast, compressed but non-exploded raw straw exhibited an RHSF value of 3.15, which is even lower than that observed with raw straw.

A substantial prior art literature exists concerning piston compression briquetting and the effects of varying process parameters. However, this concerns production of solid biomass fuel, for which the highest practicable density is desirable. Thus, applied pressures from 1000-1500 bar or even higher are routinely reported. But different considerations apply in practicing methods of the invention, where piston compression is used as a mechanical pretreatment for hydrothermal pretreatment. For practicing methods of the invention, levels of applied pressure during piston compression can be advantageously kept at levels much lower than 1000 bar. The relationship between applied piston pressure and briquette density for wheat straw using both "hydraulic" and "mechanical" systems is logarithmic. See U. Bossel (1984). In general, applied pressures less than 400 bar are sufficient to achieve densities that, while short of the desirable levels for solid fuel briquettes, are quite sufficient for practicing methods of the invention. Using piston-cylinder briquetting systems on wheat, oat, canola, and barley straw, densities of >700 kg/m3 are reported with applied pressure 125 bar, see Tumuluru et al. (2015), and 316 bar, see Adapa et al. (2009) and see Mani et al. (2006). Applied pressures of 1000 bar or higher are only needed to achieve densities approaching the dry mass density of the feedstock (i.e., density at which micro pores are completely crushed). In the case of briquettes produced by piston compression, this high density is not advantageous since it likely requires more elaborate "de-compression" at the biomass refinery, increases operating costs and very possibly destroys capillarity of the feedstock, along with the presumably related enhancement of rapid hydration swelling. However, with much smaller pellets produced using a ring die or flat die pellet mill, these same high density levels can be achieved with lower levels of applied pressure and are not disadvantageous.

Reciprocating piston compression has previously been suggested to be used as a mechanical pretreatment for biogas production from straw by Moset et al. (2015) who recommend applied pressures on the order of 2000 bar to achieve briquette densities of at least 1000 kg/m3. Reciprocating piston compression has previously been suggested to be used as a mechanical pretreatment for cellulosic ethanol production in WO2013/152771, which claims that a "mechanical steam explosion" is achieved at applied pressure from 500-3000 bar. Even if such a "mechanical steam explosion" effect was possible to achieve, this would be disadvantageous since this would by definition destroy the fiber structure, which would be expected to diminish enhancement of rapid hydration swelling. Thus, in some embodiments, the straw feedstock has been subject to piston compression to a density of between 500 and <1000 kg/m3 using an applied pressure of <500 bar. In some embodiments, straw feedstock is compressed using piston compression or ring die or flat die pelletizing where the applied pressure is at least 250 bar, or between 250-399 bar, but less than 400 bar, or between 250-499 bar, but less than 500 bar, or less than 500 bar, or between 250-699 bar, but less than 700 bar, or between 250-999 bar, but less than 1000 bar.

The dramatic difference in hydration properties of compressed versus raw wheat straw is associated with a differential absorption of steam condensate during hydrothermal pretreatment. With raw wheat straw, steam condensate is not absorbed during pretreatment but accumulates as an external "soup." In contrast, with compressed wheat straw, steam condensate is actively absorbed during pretreatment. As a consequence of this differential absorption, the effective DM content during pretreatment is reduced with compressed straw, relative to raw straw. For example, comparing raw and compressed straw pretreated at initial DM 40%, because of differential absorption of condensate, the intra-fiber solution chemistry in compressed straw is more dilute by a factor of at least 1.3×. And this is a conservative estimate of the relative dilution in compressed straw: Our results provide some indication that, possibly, this effect is compounded by a differential loss of water content during pretreatment, since some component tissues of raw straw might "leak" water content at reaction temperatures, where viscosity is reduced by a factor of more than 5 compared with room temperature.

The differential absorption of steam condensate by compressed versus raw wheat straw is associated with a diminished acidity of the soluble fraction of preteated wheat straw "whole slurry." When compressed feedstocks are pretreated at water content 60% to severity log Ro 3.76 (190° C. for 13 minutes) without agitation (including without explosive decompression), the pH of liquid fraction pressed from the pretreated material is typically at least 0.3 pH units higher than with raw wheat straw treated equivalently in the same pretreatment system. This differential acidity cannot be explained by a simple dilution effect of the increased water content in compressed straw arising from differential steam condensate absorption.

While the origins of this differential acidity are not yet understood, it is conceivable that differential effective DM content during pretreatment alone accounts for the effect: As might be expected from the term "hydrothermal," water content plays a critical role in pretreatment chemistry. See Ibbett et. al (2011) and see Ibbett et al. (2014). As the term "autohydrolysis" implies, release of acetic acid from the biomass during pretreatment catalyses additional release of acetic acid, since hemicellulose hydrolysis results in acetic acid release. Without wishing to be bound by theory, it is reasonable to presume that, because of the lower effective water content in raw straw during pretreatment compared with compressed straw, on a molar basis, acetic acid released from raw straw has an enhanced catalytic effect because of the increased concentration and resulting decreased pH. In this manner, the difference in pH at the end of pretreatment compared with compressed straw is greater than can be explained by dilution alone because more acetic acid is released from raw straw. The differential release of acetic acid could also be associated with an increased incidence of acidic byproducts. It is well established that many of the reactions whereby fermentable C5 sugars are degraded into unwanted byproducts are acid catalysed, and that some degradation products are themselves acidic. For example, degradation of C5 sugars into "pseudo-lignin" is acid catalysed. See Sannigrahi et al. (2011) and see Kumar et al (2013). Note that the acid-catalysed degradation of C5 sugars into "pseudo-lignin" is disadvantageous, not only because fermentable C5 sugars are lost, but also because pseudo-lignin inhibits cellulase enzymes and can be biologically inert in anaerobic digestion of thin stillage (an important downstream process in cellulosic ethanol production).

To the extent this interpretation is correct, increased water content provides an ameliorative role in reducing C5 degradation during pretreatment. Consistent with this interpretation, there is a clear tendency in unagitated steam pretreatment whereby higher initial DM content is associated with lower pH at equivalent severity (discussed in example 5). Also consistent with this interpretation, in at least one report, where corn stover was pretreated to equivalent severity using either steam (70% DM) or liquid hot water (10% DM), C5 degradation reactions (presumably acid-catalysed) were increased by a factor of 1.6× at higher DM content. See Allen et al. (2001).

As expected, the diminished acidity observed with compressed straw is associated with decreased hemicellulose hydrolysis during pretreatment. With compressed wheat straw, pretreated at water content 60% to severity log Ro 3.76 (190° C. for 13 minutes) without agitation (including without explosive decompression), the residual xylan+arabinan content of the solid component of the pretreated material is typically >13% by weight. This is in marked contrast with ordinary raw wheat straw pretreated at water content 60% to severity log Ro 3.76 in conventional agitated autohydrolysis steam pretreatment, where residual xylan+ arabinan content of washed pretreated fibers is typically <7%. (See WO2014/019589, p. 38 and FIGS. 1 and 2).

Notwithstanding much higher percentage residual xylan content in the solid component of pretreated material from compressed feedstocks, glucose conversion yields from enzymatic hydrolysis of whole slurry subject to equivalent conditions with equivalent dose of the same commercial cellulase preparation was roughly equivalent in our experience with compressed wheat straw subject to unagitated steam pretreatment compared with raw wheat straw subject to conventional commercial autohydrolysis steam pretreatment at equivalent severity (explained in Example 6).

In earlier years, degree of hemicellulose hydrolysis achieved during pretreatment was considered a measure of successfulness. Thus, higher residual xylan content in pretreatment was considered disadvantageous. But exactly how much hemicellulose needs to be hydrolysed in order to increase accessibility of cellulose strands to productive enzyme binding depends upon the properties of the cellulase enzyme mixture applied and, possibly, also upon the initial condition of the feedstock before pretreatment, i.e. whether it had been compressed. Using advanced generation cellulase enzyme blends, much higher levels of residual xylan content are permissible than was previously considered manageable. Any advantage of increased degree of hemicellulose hydrolysis is, in any case, offset by the related increased degradation of fermentable C5 sugars to unwanted byproducts.

As expected, the diminished hemicellulose hydrolysis observed with compressed straw is associated with decreased degradation of fermentable C5 sugars during pretreatment. With compressed wheat straw, pretreated at water content 60% to severity log Ro 3.76 (190° C. for 13 minutes) without agitation (including without explosive decompression), the total loss of fermentable C5 sugars to unwanted byproduct reactions is <15% (as discussed in example 7). This is in marked contrast with ordinary raw wheat straw pretreated at water content 60% to severity log Ro 3.76 in conventional agitated autohydrolysis steam pretreatment, where total loss of C5 sugars to unwanted byproduct reactions is typically on the order of 35%. (See WO2014/019589, p. 38 and FIGS. 1 and 2).

In light of our results, it is reasonable to suggest that acetic acid released during pretreatment is important primarily in a negative sense. This is consistent with reports that C5 degradation during "autohydrolysis" pretreatment can be reduced without detriment to final glucose yields from enzymatic hydrolysis simply by maintaining pH on the order of 5. See reports of dramatically improved C5 recovery where a small quantity of NaOH is added before liquid water pretreatment to neutralize increased acidity due to acetate release during pretreatment Li et al. (2014) (corn stover) and Yao et al. (2015) (sugar cane bagasse).

The advantages of reduced C5 degradation which can be obtained using compressed feedstocks are expected to be lost or at least diminished if the material is subject to agitation during pretreatment. At any given level of DM content and severity, the final pH of raw wheat straw in unagitated steam pretreatment is consistently higher in our experience than reported values for raw wheat straw pretreated on similar scale and under conditions that were equivalent, except that removal from the reactor was by explosive release (i.e., "steam explosion"). When small quantities of wheat straw were pretreated at water content as high as 77% to severity log Ro 3.75 (190° C. for 13 minutes) in a simple steam chamber without agitation and without explosive decompression (as discussed in example 5), the pH of liquid fraction pressed from the pretreated material was consistently above 4.0. In small experimental systems with similar quantities of wheat straw pretreated at about 80% water content using steam explosion, the pH of the soluble component is consistently around 3.8. See e.g. Jurado et al. (2009); and see Ballesteros et al. (2006); and see Alvira et al. (2011).

Direct mechanical agitation during pretreatment clearly effects the degree of hemicellulose hydrolysis and the related production of hemicellulose degradation products. In a direct comparison of identical feedstocks subject to identical pretreatment severity using different reactor configurations in a dilute acid pretreatment regime for corn stover, biomass processed using an essentially unagitated autoclave system with non-explosive pressure release exhibited much higher residual xylan content (9%) compared with that processed using steam explosion (4.8%) or using a well agitated horizontal reactor with a transport screw (3.2%). See Wang et al. (2014); and see Ciesielski et al. (2014).

Unagitated steam pretreatment has not previously been considered advantageous. To the contrary, agitation has previously been considered critical. Lischeske et al. (2016) conclude that "mechanical disruption," provided either by steam explosion or by action of a transport/compression screw, is "important" for improved pretreatment. Where lignocellulosic biomass is steam pretreated at low solids loading, "mixing" is not particularly important. However, for steam pretreatment at high solids loading>20% with uncompressed feedstocks, mixing and transfer phemonena are critically important, as discussed in a recent review by Zhang et al. (2016). Particularly important is mass and heat transfer from steam to solid lignocellulosic biomass. Chemical mechanisms of pretreatment itself and of mass and heat transfer from steam to wetted lignocellulosic biomass are not well understood. Elaborate mixing is employed in commercial autohydrolysis pretreatment systems for cellulosic ethanol plants, either as single stage, e.g. METSO™, or two stage, e.g. ANDRITZ™, systems. Thus conventional steam pretreatment reactors for lignocellulosic biomass processing have previously relied on some form of agitation. An unrelated disadvantage of continuous horizontal reactors equipped with a transport screw which can be avoided using unagitated batch reactors is that residence time of biomass in the pretreatment can be surprisingly variable. Most practitioners previously assumed that residence time in such reactors was strictly determined by rotation rate of the transport screw. But recent careful experimental studies have demonstrated that this is not actually the case—back mixing occurs such that mean residence time in such reactors can be as much as 40% longer than expected. See Sievers et al (2016).

At least for purposes of producing ethanol or other fermentation products, it is not practical to process ordinary raw feedstocks on commercial scale using unagitated hydrothermal pretreatment. Only an impractically low biomass density could be achieved within such a reactor without some form of compression. And in any case, raw straw is prone to uneven "cooking," as discussed in example 3. For example, when ordinary raw wheat straw is subject to unagitated steam pretreatment in "large" quantity (more than 5 kg DM content), the pretreated straw is typically heterogeneous, with some portions highly cooked, and having lower DM content, while other portions are less cooked and have higher DM content. It is reasonable to speculate that this underlying heterogeneity is no longer apparent and possibly no longer significant after steam explosion. As a practical matter, in a highly specialized and sensitive process such as enzymatic hydrolysis and fermentation to ethanol, extremely uneven "cooking" is undesirable for process control. Although in the case of a comparatively insensitive general anaerobic digestion to biogas, pretreatment heterogeneity may be less significant. For such processes, some net advantage of reduced C5 degradation can probably be obtained using ordinary raw straw simply by avoiding explosive release from an otherwise unagitated pretreatment system. Thus in some embodiments, the straw feedstock is subject to hydrothermal pretreatment "as is," without prior mechanical compression.

In contrast with raw straw, compressed straw can be homogeneously pretreated in an unagitated system. Either by direct absorption of steam condensate in the case of pre-wetted feedstocks or by homogeneous rapid absorption of water content added at reactor temperature and pressure, unagitated hydrothermal pretreatment of compressed straw provides homogeneous "cooking." Without wishing to be bound by theory, we believe that the dramatic alteration in hydration properties associated with compression also affects the highly water-dependent chemistry of autohydrolysis pretreatment in ways that are not yet understood.

The technical reasons for heterogeneity of raw straw "cooking" in an unagitated steam pretreatment system are not yet understood. At first glance it might be assumed that, given its very slight thickness, wetted straw biomass should come to reactor temperature very quickly and comparatively homogeneously in high pressure steam. Yet even in some agitated continuous steam pretreatment reactors, a mass-dependent heterogeneity of "cooking" has been observed (i.e., the greater the mass of feedstock within the reactor, the greater the degree of heterogeneous "cooking").

It has commonly been assumed that the factor which determines effectiveness of steam pretreatment is the "severity" [as given by log Ro where Ro=(residence time in minutes)*EXP(reaction temperature in ° C.−100/14.75)]. But while lignin melting is indeed a comparatively straightforward consequence of reactor temperature alone, hemicellulose hydrolysis is much more complex. Detailed thermodynamic studies of "autohydrolysis" steam pretreatment document a critical role for water-mediated reactions in hemicellulose hydrolysis. See Ibbett et. al (2011) and see Ibbett et al. (2014). Scanning calorimetry studies indicate that a series of initial endothermic events precede a sustained, water-mediated exothermic process associated with hemicellulose hydrolysis. See Ibbett et al. (2011), p. 9274-9275. Water is proposed to be not only a reactant in hemicellulose hydrolysis but also its principal catalyst. Our results indicate that in direct comparisons with raw straw in an equivalent unagitated experimental system, compressed straw behaves as if it had been pretreated to lower severity, notwithstanding equivalent temperature, residence time and enzymatic hydrolysis yield. This appears to be a consequence of the dramatically altered hydration properties of compressed straw.

During the initial heating of wetted biomass within a pretreatment reactor, steam heat-transfer could be expected to occur preferentially at points of lowest temperature. Micro-local temperature gradients could be formed during initial heating of raw straw. The series of endothermic events which precedes sustained exothermic hemicellulose hydrolysis might occur differentially between different tissue components of raw straw. Conceivably there could be a net enthalpy of "cooking" during steam pretreatment (excess heat required beyond heating wetted biomass to reactor temperature), which might vary between different tissue components depending on biomass structural properties, water content, and inherent water mobility/effective diffusion, exacerbating any underlying micro-local temperature gradients. Some authors report considerable net enthalpy of "cooking" in some experimental systems. See e.g. Kling et al. (1987) reporting steam consumption in sugar cane bagasse pretreatment of 1.8-1.9× the calculated theoretical level. Differential activity of endothermic reactions in different tissue components might lead to a situation in which heat-consuming reactions create temperature gradients and attract steam condensation while other tissue components come to reactor temperature indirectly by conduction.

The mechanism of steam heat-transfer to wetted biomass also might differ between different tissue components of raw straw. Pure physical studies of steam heat transfer distinguish between two different modes—a dropwise condensation heat transfer (DWC) mode, which has an order of magnitude greater heat transfer coefficient, and filmwise heat transfer (FWC), which is what eventually occurs as individual droplets combine to form a generally wetted surface. Removal of condensate from the surface of the heated material by capillary action of the material improves the heat transfer rate from dropwise mode and prevents its transition to filmwise mode. See Ghosh et al. (2014).

The very significant advantage of improved C5 recovery at roughly equivalent glucose conversion can be obtained where compressed feedstocks having either a time to swelling factor of less than 12.0 or a rapid hydration swelling factor of at least 7.0 or both are subject to hydrothermal pretreatment using an unagitated reactor system. As will be readily understood by one skilled in the art, the exact parameters of hydrothermal pretreatment in terms of water content, temperature and residence time can be optimized using routine experimentation with whatever enzyme mixture and fermentive organism is intended to be used. For example, for purposes of fermentation to ethanol, wheat straw that has been hammer milled to lengths between 10-20 mm, then compressed to a density of 750 kg/m3 can be effectively pretreated where temperature is between 186 and 191° C. and residence time is between 10-20 minutes. In some embodiments, the compressed feedstock is hydrothermally pretreated to severity log Ro between 3.65 and 4.20 or between 3.5 and 4.0. In some embodiments, the compressed feedstock is hydrothermally pretreated at a pH between 5.0 and 8.0, or between 4.0 and 9.0, or between 3.0 and 10.0 In some embodiments, residence time at a temperature between 160° and 220° C. is less than 60 minutes, or between 1 and 60 minutes, or between 2 and 120 minutes. In some embodiments, maximum temperature within the reactor may briefly exceed 220° C. but is less than 230° C., or less than 225° C., or less than 221° C.

In some embodiments, hydrothermal pretreatment is conducted as a semi-continuous process involving sequential operation of a simple, unagitated reactor in batch-mode. Such a reactor can simply be filled with biomass that has been previously mechanically compressed and then pretreated at appropriate temperature and pressure. Ideally, water content required for efficient hydrothermal pretreatment can be added inside the reactor at reaction temperature and pressure. This is practical with compressed feedstocks because they absorb water very quickly and very homogeneously even at room temperature, much less at temperatures between 160-220° C. In some embodiments, compressed straw is introduced into the reactor dry having water content<25% by weight, or <10%, or <8%, after which water is added within the pressure reactor at a temperature between 100-220° C. sufficient to adjust DM content of the compressed biomass to between 15-50% by weight after which a temperature of between 160-220° C. is maintained for between 1 minute and less than 60 minutes, or between 2 minutes and 120 minutes. In some embodiments, compressed biomass is "pre-wetted" prior to hydrothermal pretreatment. Compressed feedstocks suitable for practicing methods of the invention will, with time, at room temperature, become comparatively homogeneously wetted. In some embodiments, the compressed feedstock is added to a quantity of water sufficient to achieve a desired DM content and allowed to equilibrate without mixing for a time between 10 minutes and 60 minutes, or between 11 minutes and 120 minutes, or between 20 minutes and 240 minutes. In some embodiments, feedstocks may be wetted to appropriate water content by soaking and pressing or by other means including but not limited to those described by WO2009/125292. Water content of the feedstock during pretreatment should typically be at least 50% w/w. However, because compressed feedstocks absorb steam condensate, appropriate water content for "pre-wetting" can be significantly lower than the determined optimal water content for pretreatment. Methods of the invention can still be practiced when water content of the feedstock during pretreatment is sub-optimal, as low as 40% or even 30%. In some embodiments, water content during pretreatment can be at least 60% w/w, or between 50-65%, or between 60-70%, or between 50% and 85%. In some embodiments, initial water content at the time of exposure to mass and heat transfer from added steam or hot water can reflect a wide range of conditions, depending on whether water is added within the reactor when it is pressurized and can be 50% w/w, or between 50-65%, or between 50-70%, or at least 40% or at least 30%, or between 10% and 20%, or not more than 10%, or not more than 15%, or not more than 20%. In some embodiments, compressed feedstock is loaded into an unagitated hydrothermal pressure reactor with packing density in the occupied reactor volume between 0.08 and 0.15 kg DM/liter occupied reactor volume, or between 0.10 and 0.16, or between 0.12 and 0.25, or between 0.20 and 0.30, or between 0.15 and 0.40. In some embodiments, the pressure reactor filling level is such that the occupied reactor volume is between 40 and 50% total internal volume, or between 45 and 60%, or between 50 and 70%, or between 60 and 75%, or between 35 and 99%. In some embodiments, hydrothermal pretreatment is conducted in batch-mode either as individual batches or in sequential batches in a semi-continuous process with average quantities of biomass in each batch of at least 5 kg DM content, or at least 8 kg, or at least 25 kg, or at least 100 kg, or at least 500 kg, or at least 750 kg, or at least 1000 kg, or at least 2000 kg, or at least 3000 kg. Where pre-wetted feedstocks are used, the steam source applied in a semi-continuous process is advantageously able to deliver within 15 seconds, or within less than 60 seconds, or within less than 90 seconds, a quantity of steam sufficient to heat the feedstock and any associated water content to the desired temperature. Typically this can be achieved using a reasonably small boiler and a steam accumulator tank. For example, a 200 m3 batch reactor can be effectively and advantageously run semi-continuously with a cycle time of 2.0 hours to pretreat compressed straw pre-wetted to 60% water content to log Ro 3.76 at 190° C. with a net throughput of 8.3 tons DM/hour where the reactor filling level is 52% and packing density in the occupied reactor volume is 0.16 kg DM/m3 using a 3 megawatt (MW) boiler equipped with a 250 m3 steam accumulator designed for 20 bar pressure, where accumulator capacity for the 20 bar-12 bar pressure drop is at least 43 kg steam/m3. See Sun et al. (2017) and see Steinman and Eck (2006). In some embodiments, at the end of pretreatment, steam pressure can be vented to a collection system and used for other processes. With low pressure within the pressure reactor, the bottom valve can be opened and the pretreated biomass purged using steam or pressurized air. In some embodiments, reactor pressure at the end of pretreatment is vented to an over-pressure of not more than 4 bar after which this over-pressure is used to purge pretreated biomass from the reactor. In some embodiments, an over-pressure of not more than 4 bar is used to purge pretreated biomass from the reactor to an intermediate pressure above atmospheric. In some embodiments, an over-pressure of not more than 4 bar is used in combination with washing with water content to purge pretreated biomass from the reactor, which effectively dilutes DM content of the pretreated whole slurry, as eventually required for enzymatic hydrolysis. In some embodiments, washing with water content is used to purge pretreated biomass from the reactor without concurrent use of over-pressure.

One skilled in the art will readily conceive a variety of different reactor configurations that permit operation in unagitated batch-mode. One such reactor is shown in FIG. 2. As shown in cross-section, the reactor comprises a fustoconical pressure tank (2) mounted on a support structure (10) such that its central axis is inclined relative to vertical. An inlet valve (1) is situated in the highest portion and an outlet valve (3) is situated in the lowest portion of the tank (2) as oriented on the support structure (10). The tank is fitted with an inlet (9) through which alternatively steam or pressurized hot water can be introduced depending on the state of an upper steam valve (7) and a lower hot water valve (8) associated with an external boiler. A stirring auger (6) having diameter 20% of the tank average diameter driven by a stirring means (5) is situated along the lower side of the inclined pressure tank (2) as oriented on the support structure (10). This system is advantageous for use with dry compressed biomass to which water content is added within the reactor when it is pressurized. For example, 1 ton DM wheat straw pellets having 95% DM content can be added through inlet valve (1) to a tank (2) having internal volume 6 m3. 1448 kg of pressurized water at 190° C. can then be introduced through inlet (9) when the hot water valve (8) is open and the steam valve (7) is closed. The pelleted straw rapidly swells in the water assisted by operation of the stirring auger (6) operating with upward turning until the biomass is homogenously wetted to 40% DM at a temperature of approximately 147° C. The pressure reactor filling level in this case is expected to be about 80% and the packing density in the occupied reactor volume about 0.20. After the compressed biomass is homogeneously wetted, the stirring auger (6) can be turned off, the hot water valve (8) closed and the steam valve (7) opened. Reaction temperature of 190° C. can then be achieved and maintained using steam. After the desired severity has been achieved, steam pressure can be vented through the vent valve (4) until a pressure of about 3 bar (135° C.) is reached. The stirring auger (6) can then be operated with downward turning and outlet valve (3) opened to permit removal of the pretreated biomass as a whole slurry assisted by non-explosive over-pressure. The inclined orientation of the pressure tank (2) and operation of the stirring auger (6) permit an efficient removal of compressed feedstock pretreated as described without requirement for added water content. A system comparable to that shown in FIG. 2 could alternatively be comprised of a cylindrical rather than a fusto-conical pressure tank (2), in which case the outlet valve (3) should be situated off-center in the lowest portion of the inclined tank.

Thus in some embodiments the invention provides a hydrothermal pretreatment reactor for lignocellulosic comprising:
- a fusto-conical or cylindrical pressure tank mounted on a support structure such that its central axis is inclined relative to vertical by an angle of between 10 and 70 degrees,
- at least one inlet valve situated at the top end and at least one outlet valve situated at the bottom end of the pressure tank,
- at least one inlet for steam and at least one inlet for pressurized hot water, optionally being a single inlet that fulfills both purposes,
- a stirring auger situated along the lower side of the inclined pressure tank having diameter less than 50% of the pressure tank average diameter, and
- means for driving the stirring auger, wherein in the case of a cylindrical pressure tank the at least one outlet valve is situated off-center in the lowest portion of the inclined tank.

The terms "fusto-conical" and "cylindrical" refer to the predominant overall geometry and apply to tanks with mixed form in which some portion has an alternative form comprising no more than 30% of total internal volume or no more than 20%, or no more than 10%, or no more than 5%. Angle of inclination of the pressure tank is expressed relative to vertical, which is 0 degrees, and is between 10-70 degrees, or between 15-60 degrees, or between 15-45 or between 15-30. Diameter of the stirring auger is less than the diameter of the pressure tank. The term "average diameter" of the pressure tank refers to ½ (diameter at the top+ diameter at the bottom). In some embodiments, the stirring auger diameter is between 10-50% of the average diameter of the pressure tank, or between 10-30%. The stirring auger is situated such that the bottom of the auger is above the bottom of the pressure tank and an "internal free volume beneath the auger" exists within the tank which is defined by the internal volume beneath a horizontal plane cross section of the tank that is perpendicular to the auger central axis and that includes the lowest point of the auger. In some embodiments the internal free volume beneath the auger is at least 3% of total internal tank volume, or at least 4%, or at least 5%, or at least 7%, or at least 10%. The at least one inlet for pressurized water and the at least on inlet for steam are associated with an external boiler. The at least one pressurized water inlet can be advantageously situated in the bottom 60% of the tank volume and in some embodiments may be associated with an internal distribution/sprayer system. As will be readily understood multiple inlets for pressurized hot water and/or steam can be used. The reactor system can be scaled to any size from 400 liters to 40 m3 or 100 m3 or larger. For example, with a cycle time of 15 minutes, a reactor filling level of 85% and packing density in the occupied reactor volume of 0.25, a 6 m3 system can process a throughput of at least 5 tons DM per hour. Even for such comparatively small systems, large volumes of pressurized hot water will be introduced quickly such that the at least one inlet for pressurized water should typically be at least 7.5 cm diameter, or at least 10 cm, or at least 12 cm. As will be readily understood, the vent steam recovered through vent valve (4) can be used for a variety of purposes including pre-heating incoming compressed straw, forming and pre-heating steam or hot water for subsequent cycles, or other biorefinery processes. Similarly steam lost through outlet valve (3) can be recovered in a cyclone or other system. In some embodiments, the reactor may include an inlet for lower pressure water to be introduced as a means of assisting removal of pretreated biomass from the reactor.

Another example of a suitable reactor is an ordinary batch pulp digester commonly used in the pulp and paper industry and widely known in the art. For example, compressed straw can be pretreated in a 200 m3 batch reactor with reactor filling level 67% and packing density in the occupied reactor volume 0.16 kg DM/m3 for a total of 21.4 tons DM at 60% water content then washed with 72.3 tons water content in combination with over-pressure of not more than 4 bar to remove pretreated biomass from the reactor in the form of a whole slurry having 17% DM, which is appropriate for enymatic hydrolysis and subsequent fermentation using a C5/C6 consuming microorganism. It will be readily understood by one skilled in the art that commercially available digesters may advantageously be modified to suit particular needs. Reactor design can be optimized to permit use of non-explosive over-pressure to remove pretreated biomass, for example as described in WO2014/129910 and EP177640.

One skilled in the art will readily conceive a variety of different reactor configurations that permit continuous pretreatment of compressed straw so as to avoid agitation. In some embodiments, pretreatment is conducted as a continuous process. For example, in some embodiments, compressed straw feedstocks are continuously processed using the reactor system described in WO2015/172787, which avoids explosive release or other agitation of the feedstock during transport through the reactor. Semi-continuous process embodiments can still be advantageous, because the capital expense and risk of process bottlenecks are thereby reduced. Depending on the total throughput desired, the economies of scale and energy savings achieved using continuous reactors may not outweigh these benefits of simplicity and lower capital cost achieved with semi-continuous systems.

It will be readily understood by one skilled in the art that features of the various embodiments described can be combined. For example, any of the listed conditions for time to swelling factor, rapid hydration swelling factor, particle size, moisture content, or compression of structural wall thickness, can be applied to any means of compression with any applied pressure to produce any straw feedstocks compressed to any density that can be pretreated in individual or sequential batches in any quantity in semi-continuous process or in continuous processing using any reactor that avoids agitation of the feedstock at any pH, severity, reactor packing, reactor filling or water content introduced by any combination of prewetting and/or addition inside the reactor when it is pressurized.

EXAMPLES

1. Structural Changes of Wheat Straw Fibers During Compression.

Loose raw wheat straw having about 10% dry matter content was processed using both a shredder and a hammer mill to produce straw pieces about 10-20 mm long. The shredded, milled straw was then compressed using a reciprocating piston compression system provided by C.F. NIELSEN™. Wheat straw pieces were compressed to a specific density of approximately 750 kg/m3 with an applied pressure of about 350 bar.

Individual fibers from the compressed wheat straw were analysed for structural changes. Of the various component tissues in wheat straw, internodes were the most easily distinguishable by visual inspection.

Accordingly internodes were used as the basis for structural comparison between raw and compressed fibers.

Raw straw internodes were sliced longitudinally to permit measurement of structural wall thickness. Compressed internodes could not be separated in this manner and were measured as double-thickness walls. Thickness measurements were made using a micro caliper.

Raw wheat straw ½ internode structural wall thickness×2 (N=18) Mean 0.83 mm+/−SEM 0.1

Compressed wheat straw internode structural wall thickness (N=18) Mean 0.36 mm+/−SEM 0.06

The structural wall thickness of compressed internodes was significantly reduced relative to the structural wall thickness of raw straw internodes (t, $p<0.01$) by an average of 2.3×. This indicates that during compression to 0.75 kg/L fiber structure was significantly crushed above and beyond removal of air in straw macro lumen and between macroscopic particles.

2. Differential Water Absorption Properties of Compressed Wheat Straw at Room Temperature.

Compressed wheat straw prepared as described in example 1 exhibits differential water absorption properties at room temperature compared with raw straw. This is obvious to the naked eye. FIG. 1 shows the behavior of 6 g each of ordinary raw wheat straw and compressed wheat straw when placed in tap water at room temperature. The nominal apparent volume of each is shown at 0, 10 and 30 minutes at room temperature. As shown, the compressed straw rapidly absorbs water and becomes swelled to about ½ the nominal apparent volume of the raw straw, while the apparent volume of raw straw is largely unchanged during the same time frame.

This differential water absorption effect was quantified as a "rapid hydration swelling factor (RHSF)" determined as follows: A tested feedstock was first dried by warming at 110° C. for 60 minutes. 4 g of the dried feedstock was mixed with 125 g of water at room temperature in a glass jar that was covered with a metal sieve having average aperture area about 16 mm^2. The weight of the glass jar with sieve cover was determined before the test. The feedstock with water was allowed to sit for 30 minutes in the glass jar with sieve cover. After 30 minutes the glass jar was inverted so that free water passed by gravity through the sieve cover for a period of 1 minute whereas wetted feedstock was retained by the sieve cover. Total wet weight of the wetted feedstock was then determined. The "rapid hydration swelling factor" was expressed as the ratio of wet weight/dry weight of the tested feedstock sample where wetting was determined as described.

Raw wheat straw—from 4.0 g dry to 17.8 g wet+/−0.2 g (N=4), RHSF 4.45+/−SEM 0.05

Compressed wheat straw—from 4.0 g dry to 38.7 g wet+/−0.1 g (N=4), RHSF 9.68+/−SEM 0.03

Compressed wheat straw rapid hydration swelling factor was significantly increased, more than 2×, relative to that observed using raw straw (t, $p<0.001$).

3. Differential Behaviour of Compressed Wheat Straw During Unagitated Steam Pretreatment—Homogeneous "Cooking."

Compressed wheat straw prepared as described in example 1 exhibits differential homogeneity of "cooking" in unagitated steam pretreatment compared with raw straw. This is obvious to the naked eye.

Pretreatment experiments were conducted using a 20 L reactor chamber insulated by aluminum foil and fiber glass and sealed by a heavy, gasket lined lid. The system was equilibrated to reactor temperature prior to experiments. Feedstocks having about 90% dry matter content by weight were soaked in an excess of water (>23× by weight) for 24 hours (raw) or for 2 hours (compressed). The same "batch" of wheat straw was used both for raw straw and compressed straw samples. Soaked feedstocks were then packed into a cylinder having diameter about 10 cm and pressed using a pressurized piston with applied force (different for raw and compressed feedstocks) between about 6-8 tons sufficient to render a pressed, soaked feedstock with dry matter (DM) content of approximately 40% by weight.

Soaked and pressed feedstocks having about 40% DM were loosely packed (500-600 g wet weight) within a wire-mesh basket having internal volume about 2 L. The basket was equipped with a cover to prevent dripping into the pretreated biomass of steam condensate associated with heating the reaction vessel. The covered wire basket containing soaked and pressed feedstock was placed within a pressurization chamber and then pressurized to about 12.5 bar (190° C.) for 12.9 minutes (log Ro 3.76) with saturated steam using a steam generator having a capacity of 50 kg/h. When the pressurization chamber was depressurized, water content not associated with fibers was boiled off.

FIG. 3 shows visual appearance of raw wheat straw after unagitated steam pretreatment to log Ro 3.76. FIG. 4 shows visual appearance of briquetted wheat straw after unagitated steam pretreatment to log Ro 3.76. FIG. 5 shows differentially pretreated component tissues from raw straw subjected to unagitated steam pretreatment to log Ro 3.76. As shown in FIGS. 3 and 4, the visual appearance of raw wheat straw and compressed wheat straw are clearly different after equivalent steam pretreatment to log Ro 3.76 using this system. Raw straw appears to be unevenly "cooked," with some component tissues appearing yellowish in color while other component tissues appear "cooked" to the characteristic dark brown of straw pretreated to high severity. In contrast, compressed straw appears to have been "cooked" comparatively homogeneously but to lower severity.

With compressed straw, it was not possible to distinguish appreciably different color amongst the component tissues by visual inspection. However, as shown in FIG. 5, with pretreated raw straw, tissues having distinctly different appearance characterised by a yellow compared with brown color were separated by visual inspection. Dry matter content of the material was determined by the average of triplicate measurements of loss of weight from heating at 110° C. The soaked and pressed raw straw before pretreatment had about 40% DM. After pretreatment, the yellow component of the pretreated raw straw had 45.6% DM compared with 39.1% DM in the brown component. Conceivably, at reactor temperature where water viscosity is reduced, some water content might "drip" out of some component tissues in raw straw during pretreatment.

4. Differential Behaviour of Compressed Wheat Straw During Unagitated Steam Pretreatment—Differential Absorption of Steam Condensate.

The differential water absorption properties of compressed straw prepared as described in example 1 compared with raw straw observed at room temperature are associated with a differential absorption of steam condensate during steam pretreatment.

Pretreatment experiments were conducted essentially as described in example 3 using a 20 L scale system, operated in batch mode. Feedstocks were soaked in an excess of water (>23x by weight) for 24 hours (raw) or 2 hours (compressed). Soaked feedstocks were then packed into a cylinder and pressed using a pressurized piston with applied pressure different for raw and compressed feedstocks to achieve final equivalent dry matter content. A range of different dry matter contents were studied between 23-43%. In individual comparative experiments, equivalent dry matter content was used for raw straw and for compressed straw. Additional experiments using compressed straw alone were also conducted to confirm observations.

Soaked and pressed feedstocks having between 23-43% DM were placed loosely packed (250-300 g wet weight) within a wire-mesh basket having internal volume about 1 L. The basket was equipped with a cover to prevent dripping into the pretreated biomass of steam condensate associated with heating the reaction vessel. The covered wire basket containing soaked and pressed feedstock was placed within a pressurization chamber and then pressurized to about 12.5 bar (190° C.) for 12.9 minutes with saturated steam using a steam generator having a capacity of 50 kg/h. When the pressurization chamber was depressurized, water content not associated with fibers was boiled off.

Dry matter content of the soaked and pressed biomass before and after pretreatment was determined by the average of triplicate measurements of loss of weight from heating at 110° C. Averaging across all dry matter levels tested in individual comparative experiments, there was no significant difference overall in DM content of raw wheat straw [34.0%+/−SEM 3.5% (N=5)] and compressed wheat straw [33.5%+/−SEM 2.2% (N=11)]prior to pretreatment.

In order to minimize evaporative loss of water content, pretreated material was immediately removed from the reactor after depressurization, sealed within a plastic bag and allowed to equilibrate with room temperature for at least 2 hours prior to determination of dry matter content.

Based on the observed difference between initial dry matter content and dry matter content after pretreatment, the total change in water content during pretreatment was determined and expressed as a percentage of the initial water content:

Raw wheat straw % change in water content during PT −12.5%+/−SEM 7.5% (N=5)

Compressed wheat straw % change in water content during PT+14.5%+/−SEM 5.3% (N=11)

As shown, there was a highly significant difference in percent change of water content during pretreatment between raw wheat straw and compressed wheat straw (t, p<0.01). Interpretation of this result is somewhat complex in that, in this experimental system, at the end of pretreatment, all water content that is not associated with fibers is boiled off during depressurization of the reactor chamber.

The total theoretical expected gain in water content during pretreatment can be readily estimated, assuming that there exists no net "enthalpy of cooking" and that the steam condensate absorption is determined solely by the cost of heating the biomass and associated water content to reactor temperature. However, it should be noted that the assumption of no net "enthalpy of cooking" very clearly might not be correct. Some authors report considerable net "enthalpy of cooking" in some experimental systems. See e.g. Kling et al. (1987). With the caveat that the estimated expected gain in water content might be an underestimate, consider 1 kg wet weight biomass at 33% dry matter content:
(170° difference from room to 190)*(4.18 kJ−1/(kg K) water CP at 20)*(0.67 kg water)=−0.476 MJ
(170° difference from room to 190)*(1.3 kJ−1/(kg K) straw CP at 20—from Dupont et al. (2014))*(0.33 kg straw)=−0.073 MJ
INITIAL HEATING COST −0.549 MJ steam, where 2287 kJ/kg steam at 190° C.
INITIAL STEAM CONDENSATE −0.549 MJ=+0.240 kg stream initially condensed
(90° difference from reactor to 100)(4.18 kJ−1/(kg K) water CP at 20)(0.240+0.67 kg water)=+0.342 MJ
(90° difference from reactor to 100)(1.3 kJ−1/(kg K) straw CP at 20)(0.33 kg straw)=+0.039 MJ
EVAPORATION ON DEPRESSURIZATION+0.381 MJ, where 2287 kJ/kg steam at 190° C.
LOSS OF CONDENSATE ON DEPRESSURIZATION+ 0.381 MJ=−0.17 kg condensate evaporated at depressurization
TOTAL EXPECTED GAIN IN WATER CONTENT at 33% DM: (0.67+0.240−0.17)/(0.67)=+10.4%.

In this experimental system, raw straw is observed to actually lose water content during pretreatment (−12.5%). As explained this result is difficult to interpret in this experimental system. However, it is clearly consistent with a "dripping out" effect, whereby water content actually drips out from raw straw at reactor conditions of 190° C. This is not inconceivable, since the viscosity of liquid water at 190° C. is reduced by a factor of at least 5 compared with viscosity at room temperature.

Compressed straw is observed to increase water content during pretreatment (+14.5%) by approximately the margin expected due to absorption of steam condensate. Expressed in absolute terms, compressed straw experienced an increase in water content relative to raw straw of +27.0% which means that compressed straw experienced a considerably lower effective dry matter content during pretreatment.

These results are consistent with our visual observation of the behaviour of raw straw in this reactor system and indicate that compressed straw readily absorbs steam condensate under reactor conditions. In contrast, with raw straw, steam condensate is not readily absorbed but tends to form an external pool or "soup" under reactor conditions. As a consequence of the differential absorption of steam condensate, the effective dry matter content during pretreatment is reduced with compressed straw, relative to raw straw.

5. Differential Behaviour of Compressed Wheat Straw During Unagitated Steam Pretreatment—Lower Acidity of Soluble Fraction.

During pretreatment experiments in which raw wheat straw was compared with compressed wheat straw prepared as described in example 1 at equivalent initial DM at log Ro 3.76 (190° C. for 12.9 minutes), pH of the soluble fraction in pretreated "whole slurry" was consistently lower with raw straw.

Samples were prepared and pretreated as described in example 4. Averaged across all dry matter levels tested in individual comparative experiments, there was no significant difference prior to pretreatment overall in DM of raw wheat straw [31.9%+/−SEM 3.9% (N=7)] and compressed wheat straw [33.0%+/−SEM 2.1% (N=16)]. Initial pH was estimated for samples of raw (90% DM) and compressed (90% DM) straw to which water was added to make a 40% DM sample. The samples were then centrifuged and pH of the free water content measured. Compressed straw was initially slightly more acidic (pH 6.60+/−0.005, N=2) than raw straw (pH 7.21+/−0.01, N=2).

After pretreatment, after equilibration to room temperature, a sample of the pretreated material was removed, packed into a cylinder and pressed using a pressurized piston to extract a sample of soluble fraction from the pretreated "whole slurry." The pH of this extracted liquid fraction was determined.

(DM Range 23-43%)

Pretreated raw wheat straw soluble fraction pH—4.05+/−SEM 0.08 (N=7)

Pretreated compressed straw soluble fraction pH—4.43+/−SEM 0.02 (N=16).

Taken as an average over the range of different dry matters tested, pH of the soluble fraction from pretreated raw straw was significantly lower by more than 0.3 pH units compared with pH of soluble fraction from pretreated compressed wheat straw (t, $p<0.001$). This effect could not be explained by a simple dilution factor, accounting for the increased water content of soluble fraction arising from increased absorption of steam condensate with pretreated compressed straw.

A clear tendency was observed whereby higher initial dry matter content was associated with lower pH. Accordingly, comparative experiments were repeated for confirmation of the overall effect at initial DM 40%.

(DM 40%)

Pretreated raw wheat straw soluble fraction pH—3.81+/−SEM 0.03 (N=3)

Pretreated compressed straw soluble fraction pH—4.24+/−SEM 0.01 (N=3).

Again, pH of the soluble fraction from pretreated raw straw was significantly lower by more than 0.3 pH units compared with pH of soluble fraction from pretreated compressed wheat straw (t, $p<0.001$). Again, this effect could not be explained by a simple dilution factor, accounting for the increased water content of soluble fraction arising from increased absorption of steam condensate with pretreated compressed straw.

6. Differential Behaviour of Compressed Wheat Straw During Unagitated Steam Pretreatment—Lower Effective Severity/Reduced Hemicellulose Hydrolysis at Equivalent Reactor Temperature and at Equivalent Apparent Severity.

In initial experiments, pretreatment conditions for compressed wheat straw prepared as described in example 1 were optimized using the unagitated steam pretreatment system described here. Optimization was based on enzymatic hydrolysis yields with a second generation commercial enzyme CTEC2 ™ from NOVOZYMES™. The success criterion for optimization was that roughly equivalent glucose yields could be obtained at equivalent enzyme dose of CTEC2™ compared with those reported by a commercial competitor, INBICON™, using raw straw in a commercial, agitated, continuous steam pretreatment system.

It became apparent during the course of these optimization experiments that reactor temperatures of 185° C. were not sufficient to achieve effective pretreatment, regardless of residence time within the reactor. Optimal conditions were observed where compressed wheat straw was subjected to unagitated steam pretreatment at 40% DM at 190° C. for 12.9 minutes (log Ro 3.76). This pretreated material could be readily hydrolyzed as whole slurry comprising both liquid and solid component. At a dose of 0.07 ml CTEC2/g glucan, the hydrolysis yield in theoretical glucose conversion obtained in 96 hours using this material from our unagitated system was equivalent to that reported by INBICON™ at a dose of 0.08 ml CTEC2/g glucan using whole slurry from ordinary straw pretreated to approximately log Ro 3.75 in a conventional agitated reactor. See INBICON™ international patent application WO2014/019589, example 4, FIG. 5.

However, notwithstanding equivalent apparent severity expressed in terms of log Ro, the effective severity in the compressed straw pretreated with this unagitated system was much lower compared with raw straw pretreated by INBICON™ process using a conventional agitated steam reactor.

As explained by INBICON™ in the international patent applications WO2014/019589 and WO2015/014364, a measure of the effective severity of steam pretreatment is the residual xylan content of the solid fraction in the pretreated "whole slurry."

During the course of optimisation experiments with compressed wheat straw, a variety of reactor conditions were tested to achieve apparent severity log Ro between 3.8 and 4.0 at either 190° C. or at 195° C. In six independent experiments, compressed straw was soaked in an excess of water at room temperature for one hour then packed into a cylinder and pressed using a pressurized piston with applied force 6 tons to dry matter content about 40%.

Soaked and pressed compressed wheat straw having DM about 40% was placed loosely packed (250-300 g wet weight) within a wire-mesh basket having internal volume about 1 L. The basket was equipped with a cover to prevent dripping into the pretreated biomass of steam condensate associated with heating the reaction vessel. The covered wire basket containing soaked and pressed feedstock was placed within a pressurization chamber and then pressurized to about 12.5 bar (190° C.) or about 14.0 bar (195° C.) for between 10 to 22.5 minutes with saturated steam using a steam generator having a capacity of 50 kg/h.

Dry matter content of the soaked and pressed biomass before and after pretreatment was determined by the average of triplicate measurements of loss of weight from heating at 110° C. In order to minimize evaporative loss of water content, pretreated material was immediately removed from the reactor after depressurization, sealed within a plastic bag and allowed to equilibrate with room temperature for at least 2 hours prior to determination of dry matter content. After equilibration to room temperature, a sample of the pretreated material was removed, packed into a cylinder and pressed using a pressurized piston to extract a sample of soluble fraction from the pretreated "whole slurry." The pH of this extracted liquid fraction was determined.

Compressed wheat straw "whole slurry" pretreated as described was subjected to a washing protocol to obtain washed solid fraction as follows: Whole slurry was suspended with a 10× (by weight) excess of water, agitated and then centrifuged. Supernatant was decanted and the washing process repeated two additional times. Pellets in the last step were dried at 45° C.

The xylan content of washed pretreated fibers was determined as the average of triplicate determinations using the method of Sluiter A. Determination of structural carbohydrates and lignin in biomass. NREL Laboratory Analytical Procedures. 2004. National Renewable Energy Laboratory, Golden, CO, USA. Measured values of residual xylan content in washed fiber obtained with compressed wheat straw are shown below along with corresponding values obtained at equivalent severity reported by INBICON™ using raw wheat straw pretreated with a conventional, agitated reactor.

| logRo | temp | min. | pH | COMP. PT fiber % xylan | INBICON* PT fiber % xylan |
|---|---|---|---|---|---|
| 3.8 | 190 | 12.9 | 4.20 | 18.4% | ~6.0% |
| 3.9 | 190 | 17.17 | 3.93 | 14.9% | <5.0% |

| logRo | temp | min. | pH | COMP. PT fiber % xylan | INBICON* PT fiber % xylan |
|---|---|---|---|---|---|
| 4.0 | 190 | 22.30 | 3.83 | 9.0% | ~3.0% |
| 3.8 | 195 | 10.0 | 4.12 | 17.3% | ~6.0% |
| 3.9 | 195 | 12.70 | 3.98 | 11.6% | <5.0% |
| 4.0 | 195 | 15.9 | 3.83 | 8.3% | ~3.0% | from INBICON™ international patent application WO2015/014364; from FIG. 1, "Xylan number as a function of severity factor," determine xylan number for wheat straw pretreated to log Ro 3.8, 3.9 and 4.0 as about 9.0, 6.0 and 4.0 respectively; from FIG. 2, "Xylan content of undissolved solids in wt. % as a function of xylan number" determine wt. % xylan for xylan numbers 9.0, 6.0, and 4.0 as ~6.0, <5.0 and ~3.0.

As shown, the effective severity using compressed wheat straw in the unagitated steam pretreatment system is dramatically reduced compared with raw wheat straw treated in a conventional INBICON™ agitated steam reactor at equivalent log Ro. Xylan content of insoluble fiber is dramatically enhanced with compressed straw at identified optimal conditions of log Ro 3.76 (190° C. for 12.9 minutes) at which glucose hydrolysis yields using CTEC2™ were approximately equivalent to those reported with raw wheat straw pretreated to equivalent log Ro in a conventional INBICON™ agitated steam reactor.

As shown, INBICON™ pretreatment at equivalent log Ro is associated with considerably greater hydrolysis of residual xylan into C5 sugars. Free C5 sugars subsequently experience additional chemical reactions during INBICON™ pretreatment leading to formation of a wide variety of byproduct compounds, many of which exhibit inhibitory properties towards cellulase enzymes. See Rasmussen, H., et al. (2016) and see Rasmussen, H. et al. (2014).

The observed decreased effective severity with compressed straw is consistent with expectations from the observed decreased acidity of soluble fraction from pretreated compressed straw.

To quantify the difference in effective dry matter content during pretreatment between raw and compressed wheat straw, an assumption is applied that no water content "drips out" from raw straw at reactor conditions of 190° C. and that there is no net "enthalpy of cooking." As explained in example 4, these assumptions clearly might not be correct, in which case the estimated difference in effective dry matter content during pretreatment is an underestimate.

The expected increased water content due to absorption of steam condensate by compressed straw during pretreatment at 40% dry matter can be estimated as follows:
(170° difference from room to 190)(4.18 kJ–1/(kg K) water CP at 20)(0.60 kg water)=–0.426 MJ
(170° difference from room to 190)(1.3 kJ–1/(kg K) straw CP at 20)(0.40 kg straw)=–0.088 MJ
INITIAL HEATING COST –0.514 MJ steam, where 2287 kJ/kg steam at 190° C.
INITIAL STEAM CONDENSATE –0.514 MJ=+0.225 kg stream initially condensed
EFFECTIVE % DRY MATTER DURING PRETREATMENT [(0.40)/(0.40+0.60+0.225)]=32.7%

Thus, a conservative estimate of the effective difference in dry matter content during pretreatment between raw wheat straw and compressed wheat straw is 40% DM compared with 32.7% DM. As a pure question of concentration of solutes, the intra-fiber solution with compressed wheat straw is more dilute by a factor of about 1.37x. Conceivably this dilution effect and other consequences of the differences in effective dry matter content during pretreatment might account for observed differences in evolved acidity and hemicellulose hydrolysis/effective severity.

7. Differential Behaviour of Compressed Wheat Straw During Unagitated Steam Pretreatment—Increased C5 Recovery.

As a consequence of reduced hemicellulose hydrolysis at equivalent log Ro, total recovery of C5 sugars is substantially improved using compressed wheat straw prepared as described in example 1 in unagitated stream pretreatment compared with raw wheat straw in conventional agitated steam pretreatment.

Samples of pretreated compressed wheat straw "whole slurry" prepared as described in example 6 were subjected to enzymatic hydrolysis using an excess of CTEC2™ (approximately 25 FPU/g glucan). Dry matter content of samples was measured in triplicate immediately before use in enzymatic hydrolysis experiments. Wet sample was added sufficient to achieve a total of 20 g dry matter in each hydrolysis reaction. Samples were weighed in 1 L plastic capped bottles. Hydrolysis experiments were conducted in 50 mM citrate buffer at pH 5.0 at 17% DM. Hydrolysis bottles were rotated in a tumbler at 50 degrees C. with a frequency of rotation of 14 rpm for 96 hours. After hydrolysis, reaction bottles were boiled for 15 minutes. Samples of 1.5 ml were removed, centrifuged to remove suspended solids, filtered using 0.45 um filters and diluted 50× in HPLC eluant. Xylose levels were determined as the mean of duplicate HPLC measurements from duplicate hydrolysis experiments. Background xylose detected in control samples containing only enzyme mixture and buffer was subtracted and final xylose recovery expressed as g xylose released per g dry matter content in the hydrolysis reaction.

Final xylose recoveries observed in these experiments cannot be exactly expressed, because the initial xylan content of the tested straw was not directly measured. Applying an estimate that initial xylan content was 24.0%, where theoretical xylose content corresponds to 1.136 g xylose/g xylan, the observed final xylose recoveries in the enzyme overdose experiments obtained with compressed wheat straw are shown below along with corresponding C5 recovery values obtained at equivalent severity reported by INBICON™ using raw wheat straw pretreated with a conventional, agitated reactor.

| logRo | temp | min. | pH | % recov. xylose | COMP. % loss xylose | INBICON* % loss xylose |
|---|---|---|---|---|---|---|
| 3.8 | 190 | 12.9 | 4.20 | 100.0% | 0 | 37% |
| 3.9 | 190 | 17.17 | 3.93 | 85.3% | 14.7% | 50% |
| 4.0 | 190 | 22.30 | 3.83 | 81.7% | 19.3% | 67% |
| 3.8 | 195 | 10.0 | 4.12 | 86.4% | 13.6% | 37% |
| 3.9 | 195 | 12.70 | 3.98 | 78.4% | 21.6% | 50% |
| 4.0 | 195 | 15.9 | 3.83 | 39.9% | 61.1% | 67% | from INBICON™ international patent application WO2015/014364; from FIG. 1, "Xylan number as a function of severity factor," determine xylan number for wheat straw pretreated to log Ro 3.8, 3.9 and 4.0 as about 9.0, 6.0 and 4.0 respectively; from FIG. 2, "Recovery of hemicellulose after pretreatment . . . as a function of xylan number" determine total recovery as water insoluble solids (WIS) and water soluble solids (WSS) for xylan numbers 9.0, 6.0, and 4.0 as 63%, 50%, and 33%; from calculated recoveries determine % loss for xylan numbers 9.0, 6.0, and 4.0 as 37%, 50%, and 67%.

As shown, using compressed wheat straw in a simple, unagitated steam pretreatment system, C5 loss during pretreatment can be dramatically reduced compared with conventional, agitated reactors. C5 loss during pretreatment, presumably due to degradation reactions, is a severe problem in "autohydrolysis" processing, particularly with wheat straw. Elaborate schemes for minimizing C5 loss have been presented by well known competitors in the cellulosic ethanol industry, including both INBICON™ (see WO2015/014364 and see WO2014/019589) and BETA RENEWABLES™ (see WO2010/113129).

8. Homogeneity of Unagitated Steam Pretreatment of Compressed Wheat Straw on 50× Scale-Up.

Experiments were conducted using a 50× scaled-up reactor system to study the scalability of the observed capacity of compressed wheat straw prepared as described in example 1, in contrast with raw straw, to be pretreated homogeneously in unagitated steam pretreatment.

A scaled-up reactor suited for pressurization to at least 16 bar was prepared having internal volume 110 L and diameter about 60 cm. The reactor comprised two cylindrical sections wrapped with foil and fiber glass insulation joined at a flange that could be sealed using 18 large bolts. Steam from a steam generator having a capacity of 50 kg/h was fed into the reactor from the bottom. The steam stream was directed onto a splitting plate to provide even distribution of steam within reactor. The bottom of the reactor was tapered. Within the tapered bottom, a wire mesh "floor" was inserted.

Compressed straw was soaked in an excess of water at room temperature for one hour then packed in several batches into a large cylinder and pressed using a pressurized piston with applied force 6 tons to DM about 40%.

In two independent experiments, soaked and pressed compressed wheat straw having DM about 40% was placed loosely packed (22-25 kg wet weight) within a wire-mesh basket having internal volume about 100 L. The basket was equipped with a cover to prevent dripping into the pretreated biomass of steam condensate associated with heating the reaction vessel. The covered wire basket containing soaked and pressed feedstock was placed within the bottom half of the reactor, supported by the wire mesh "floor." The basket was surrounded on all sides by void volume so as to avoid any contact with the reactor walls. The top half of the reactor was then aligned with the bottom and both halves sealed with large bolts. Because of the small capacity of the steam generator, using this large quantity of biomass, pressurization to 12.5 bar (190° C.) was slow, requiring approximately 45 minutes. Reactor temperature of 190° C. was maintained for 10 minutes prior to de-pressurization. The cumulative severity expressed as log Ro for the slow heating process was not determined.

In each of two independent experiments, after de-pressurization, the sealing bolts were removed and the top half of the reactor was lifted away from the bottom half using a crane. The wire basket was removed and the top half of the pretreated material removed using a pitchfork and turned top-side down on a large plastic sheet. Handful-sized samples were quickly removed using plastic bags which were immediately sealed. Samples were taken along a radius from the outer edge, intermediate and center of the stack of pretreated material. Similar radial samples were taken from the pretreated material in the bottom half of the reactor.

For each sample, glucose hydrolysis (% theoretical conversion), dry matter content, and xylan content in washed fiber were determined. Glucose hydrolysis was determined using 5 FPU/g glucan CTEC2™ in 50 mM citrate buffer at pH 5.0 for 96 hours in duplicate hydrolysis experiments having approximately 1 g dry matter. Background glucose detected in control samples containing only enzyme mixture and buffer was subtracted and final glucose levels expressed as g glucose released per g dry matter content in the hydrolysis reaction. Percent glucose conversion was expressed as $[(0.91)*(\text{glucose g release/g DM})/0.35]$. Dry matter content was determined as means of duplicate measurements using an automated moisture analyser based on loss of weight at 105° C. Xylan content was determined in washed fibers as described in example 6.

Taking each of the triplicate determinations of xylan content as a separate n, there was no overall significant difference in fiber xylan content between the first and second experiments, 9.59% vs 10.8% N=36. But note that these levels of fiber xylan content correspond to a log Ro severity of greater than 3.9, which is well beyond the previously determined optimal condition for wheat straw, as described in example 6. Levels of enzyme inhibitors derived from C5 degradation reactions are likely increased in these samples, relative to identified optimal conditions.

Glucose conversion was slightly but not significantly different between the first and second experiments taking each of the 1 g experimental determinations as a separate n—first experiment 79.0%, +/−SEM 1.5%; second experiment 77.0+/−SEM 1.6%, t, p<0.09 N=36.

There was a slight but significant radius-dependence of DM content after pretreatment. Using individual DM determinations as the observvable, and analysing by ANOVA, the radius-dependence was—outer 33.8%+/−SEM 1.3%, middle 36.9%+/−SEM 0.6%, inner 39.4%+/−SEM 0.5%, F, p<0.001, N=24. This indicates that, because of slow heat-up time, inner portions of the biomass stack were heated in part by conduction, while outer portions of the stack were heated by direct absorption of steam condensate.

There was also a slight but significant radius-dependence of glucose conversion yield. Analysed by ANOVA, the radius-dependence of conversion yield was—outer 79.3%+/−SEM 1.4%, middle 78.8%+/−SEM 1.5%, inner 75.4%+/−SEM 1.1%, F, p<0.04, N=24. Viewed as a t test, there was a statistically significant difference in conversion yield between combined outer—middle versus inner groups, t, p<0.005, N=16/8. As expected, lower dry matter content in the outer portions of the stack was associated with more effective pretreatment and accordingly improved glucose hydrolysis yield.

There was similarly a slight radius-dependence of fiber xylan content, although its significance is less clear cut. Variability in the fiber xylan signal was extremely high. Analysed by ANOVA, the radius-dependence of fiber xylan content was—outer 10.6%+/−SEM 0.8%, middle 8.7%+/−SEM 0.4%, inner 11.2%+/−SEM 0.7%, F, p<0.04, N=36. This is at first glance difficult to interpret, since the difference between outer and middle is larger than the difference between inner and outer. However, when we compare the t test for combined outer and middle versus inner, the result aligns with the hydrolysis results—combined outer/middle 9.7% versus inner 11.2%, t, p<0.08, N=24/12.

There was a significant difference in DM content between upper and lower sections—upper 38.05%, lower 35.30% DM, t, p<0.04. This indicates that there was some migration of water content due to gravity during the course of the long pretreatment reaction.

No significant difference in glucose conversion was discernible overall between upper and lower sections—upper 78.3%, lower 78.8% conversion.

These results indicate that, notwithstanding a long heat-up time on the order of 4 times the pretreatment reaction time, which resulted in different zones of material heated by direct absorption of steam condensate (outer) compared with material heated primarily by conduction (inner), only a slight gradient in severity relative to reactor volume was observed with compressed wheat straw pretreated in an unagitated batch system. This indicates that comparatively homogenous pretreatment can be achieved with compressed straw in such a system where the steam supply is sufficient to achieve rapid heat-up of reactor contents.

9. Homogeneous Absorption of Water by Compressed Wheat Straw at Room Temperature.

Hammer milled wheat straw compressed by a ring die pellet mill from Munch-Edelstahl, GmbH, Hilden, Germany, into 8 mm press channels was obtained from X-Straw ApS, Skælskor, Denmark. Specific density 1068+/−52 kg/m3 (N=6) was determined from measurements of mass of individual pellet pieces and an estimation of the volume of each piece based on measurements of length with constant diameter 8.2 mm. DM content 93.59+/−0.15% w/w (N=3) was determined using an automated DM analyzer. A 500 ml beaker was filled with 230.5 g water at room temperature into which was placed 98.34 g straw pellets. The pellets swelled rapidly, expanding into the volume of the beaker such that free water was no longer visible and the pellet mass appeared to be homogeneously wetted after 23 minutes. After 30 minutes, DM content was determined for samples taken from the bottom and from the top of the beaker for comparison. The pellet mass was comparatively homogeneously wetted, top 29.52+/−0.62% DM (N=2), bottom 27.87+/−0.70% DM (N=2). In preparation for pretreatment experiments, a 50 liter container was filled with 34.90 liters water at room temperature into which was placed 16.0 kg straw pellets. The pellets swelled rapidly, expanding into the volume of the container in such manner as to form a dense mass of wetted, compressed straw which required forceful "stirring" with a heavy metal rod in order to be removed. After 60 minutes, the wetted compressed straw mass was removed from the wetting container and placed within a wire mesh basket specially designed to fit within the reactor described in example 8 at a packing density of 0.16 kg DM/liter basket volume. The basket internal volume was approximately 90% of the reactor internal volume. While filling the reactor basket, samples from the bottom, middle and top of the wetted compressed straw mass were compared and found to be comparatively homogenously wetted with a slight DM gradient from the bottom to the top corresponding to that observed on 500 ml scale.

10. Homogeneous Pretreatment of Pre-Wetted Compressed Straw.

The basket containing pre-wetted compressed straw prepared as described in example 9 having average DM content 29.4% (distributed within the range 27-30%) was set upon a triangular metal base within the reactor described in example 8 with a gap of about 4 cm between the walls of the reactor and those of the cylindrical basket. The reactor was then sealed, and the wetted biomass subject to pretreatment using the steam generator described in example 8. With the limited steam capacity of the system used, the pretreatment required 92 minutes. The pressure gauge on the steam generator was previously compared with direct measurements of temperature within the reactor to determine a slight correction factor. Temperature within the reactor corresponding to 160° C. was reached after 46 minutes. The target temperature of 190° C. was reached after 70 minutes. The target temperature was maintained for 10 minutes, after which the reactor was slowly depressurized to atmospheric pressure over 11 minutes. Although the target severity was log Ro 3.76, the cumulative actual severity in this case was log Ro 4.04, where each minute of the pretreatment is accounted with Ro=1 minute*EXP(reaction temperature in ° C.−100/14.75. After the basket was removed from the reactor, pretreated material was examined to determine apparent homogeneity. By visual inspection, the material was homogenously pretreated with no apparent gradient either radially or vertically, except that at the bottom ⅙ of the basket, some material was plainly differentially "cooked." This was attributed to interference caused by interaction with the pool of condensate associated with heating the steel reactor, which condensate accumulates at the bottom of the reactor's internal volume. The same experiment was conducted a second time with equivalent results.

11. Homogeneous Pretreatment of Compressed Wheat Straw where Water Content was Added Inside the Reactor when it was Pressurized.

The reactor and steam generator described in example 8 were used to test pretreatment where water content was achieved primarily by adding water content inside the reactor when it was pressurized. 5.2 kg of the dry wheat straw pellets described in example 9 having 93.6% DM (4.86 kg DM total) were loaded in a crude basket made from fine metal mesh and sealed within the reactor described in example 8. The reactor mass was approximately 358 kg such that approximately 7 kg of steam condensate was expected to accumulate in the process of bringing the reactor to 100° C. using the steam generator described in example 8. The 4.86 kg DM was thus expected to reach 40% DM on average by the time the reactor reached 100° C. The average final dry matter was expected to be approximately 28% by the time the reactor came to reaction temperature 190° C. The reactor loaded with dry pellets came to temperature 190° C. over the course of 55 minutes, after which pressure was vented to 100° C. within 7 minutes. The estimated log Ro from the reaction as run was 3.86.

In this experimental protocol, the preated pellets formed a large pile in which distinctly different regions were apparent: An apparently burnt top region 0, a lower region 1, a still lower region 2 and in the bottom ½ of the pile, two obviously different regions that were intermixed, some appearing dark blonde (region 3) others appearing dark brown and characteristically well cooked (to high severity) (region 4). Dry matter was determined as means of triplicate determinations in foil weighing pans left at 105° C. overnight. Dry matter in (3) was 23% (N=3) and in (4) was 39% (N=3), with tight replicates. In the other regions dry matters were highly variable between replicates: (0) 64.8% (N=3), (1) 87.3% (N=3), (2) 73.3% (N=3).

The crude basket used in this experimental protocol was evaginated and apparently created an effect in which condensate from the sides of the reactor was channeled into and out of distinct streams. The region 3 material appeared normally but lightly "cooked," and was likely brought to 40% DM by the time the reactor reached 100° C. The region 4 material likely accumulated water content only gradually such that it was pretreated at high temperatures at high dry matter content, which was previously shown to produced deleterious effects regarding C5 degradation.

Although it was not possible using this system to add water content quickly inside the reactor when it was pressurized, this experiment nevertheless demonstrates that normal "cooking" can be achieved in this manner.

The embodiments and examples described are exemplative only and not intended to limit the scope of the invention as defined by the claims.

Non-Patent References

Adapa, P. et al., "Compaction characteristics of barley, canola, oat and wheat straw," Biosystems Engineering (2009) 104:335-344.

Allen, S. "A comparison between hot liquid water and steam fractionation of corn fiber," Ind. Eng. Chem. Res. (2001) 40:2934.

Alvira, P. et al. "Effect of endoxylanase and alpha-L-arabinofuranosidase supplementation on the enzymatic hydrolysis of steam exploded wheat straw," Bioresource Technology (2011) 102:4552-4558.

Ballesteros, I. et al. "Ethanol production from steam-explosion pretreated wheat straw," Applied Biochemistry and Biotechnology (2006) 129-132:4996-5008.

Bossel, U. "Production and marketing of briquettised and pelletised solid biomass fuels," Bioenergy 84, volume 1, 1984.

Bychkov, A. et al. "Ultrastructural changes of cell walls under intense mechanical treatment of selective plant raw material," Biomass and Bioenergy (2012) 47:260.

Ciesielski, P. et al., "Effect of mechanical disruption on the effectiveness of three reactors used for dilute acid pretreatment of corn stover Part 2: morphological and substrate analysis," Biotechnology for Biofuels (2014) 7:47.

Dupont, C. et al., "Heat capacity measurements of various biomass types and pyrolysis residues," Fuel (2014) 114: 644-651.

Ghosh, A. et al. "Enhancing dropwise condensation through bioinspired wettability patterning," Langmuir (2014) 30:13103.

Ibbett, R. et al. "The mechanisms of hydrothermal deconstruction of lignocellulose: New insights from thermal-analytical and complementary studies," Bioresource Technology (2011) 102:9272.

Ibbett, R. et al. "The kinetics of inhibitor production resulting from hydrothermal deconstruction of wheat straw studied using a pressurised microwave reactor," Biotechnology for Biofuels (2014) 7:45.

Jurado, M. et al. "Laccase detoxification of steam-exploded wheat straw for second generation bioethanol," Bioresource Technology (2009) 100:6378-6384.

Kling, S. et al. "Enhancement of enzymatic hydrolysis of sugar cane bagasse by steam explosion pretreatment," Biotechnology and Bioengineering (1987) 29:1035.

Kumar, R. et al. "Carbohydrate-derived pseudo-lignin can retard cellulose bioconversion," Biotechnology and Bioengineering (2013) 110(3):737.

Lara-Vazquez, A. et al., "Particle size and hydration medium effects on hydration properties and sugar release of wheat straw fibers," Biomass and Bioenergy (2014) 68:67.

Li, H. et al. "pH pre-corrected liquid hot water pretreatment on corn stover with high hemicellulose recovery and low inhibitors formation," Bioresource Technology (2014) 153:92.

Lischeske, J. et al., "Assessing pretreatment reactor scaling through empirical analysis," Biotechnology for Biofuels (2016) 9:213.

Mani, S., et al., "Effects of compressive force, particle size and moisture content on mechanical properties of biomass pellets from grasses," Biomass and Bioenergy (2006) 30:648-654.

Moset. V., et al., "Optimization of methane yield by using straw briquettes—influence of additives and mold size," Industrial Crops and Products (2015) 74:925.

Rasmussen, H. et al., "Formation of degradation compounds from lignocellulosic biomass in the biorefinery: sugar reaction mechanisms," Carbohydrate Research (2014) 385:45]

Rasmussen, H. et al., "New degradation compounds from lignocellulosic biomass pretreatment: routes for formation of potent oligophenolic enzyme inhibitors," Green Chemistry (2016) DOI: 10.1039/c6gc01809b.

Rijal, B. et al., "Combined effect of pelleting and pretreatment on enzymatic hydrolysis of switchgrass," Bioresource Technology (2012) 116:36-41.

Sannigrahi, P. et al. "Pseudo-lignin and pretreatment chemistry," Energy & Environmental Science (2011) 4:1306.

Sievers, D., et al., "Online residence time distribution measurement of thermochemical biomass pretreatment reactors," Chemical Engineering Science (2016) 140:330.

Steinman, W. and Eck, M. "Buffer storage for direct steam generation," Solar Energy (2006) 80:1277-1282.

Stelte, W. et al., "Fuel pellets from biomass: The importance of the pelleting pressure and its dependency on the processing conditions," Fuel (2011) 90:3285-3290.

Stelte, W. et al., "Recent developments in biomass pelletization—a review," BioResources (2012) 7(3): 4451-4490.

Sun, W. et al., "Operation optimization of steam accumulators as thermal energy storage and buffer units," Energies (2017) 10, 17; doi:10.3390/en10010017

Tumuluru, J., et al., "Impact of process conditions on the density and durability of wheat, oat, canola, and barley straw briquettes," Bioenerg. Res. (2015) 8:388.

Wang. W., et al., "Effect of mechanical disruption on the effectiveness of three reactors used for dilute acid pretreatment of corn stover. Part 1: chemical and physical substrate analysis," Biotechnology for Biofuels (2014) 7:57.

Yao, S. et al. "Efficient extraction of bagasse hemicelluloses and characterization of solid remainder," Bioresource Technology (2015) 185:2.

Zhang, Q. et al. (2015) "Effects of ultrasonic vibration-assisted pelleting on chemical composition and sugar yield of corn stover and sorghum stalk," Renewable Energy 76:160-166

Zhang, J. et al., "Reactors for high solid loading pretreatment of lignocellulosic biomass," Adv. Biochem. Eng. Biotechnol. (2016), 152:75-90.

Zhang, Q. et al. (2017) "Investigation on characteristics of corn stover and sorghum stalk processed by ultrasonic vibration-assisted pelleting," Renewable Energy 101: 1075-1086]

Patent References

WO2010/113129; US2010/0279361; WO 2009/108773; US2009/0308383; U.S. Pat. No. 8,057,639; US2013/0029406 WO2014/019589; WO2015/014364; WO2013/152771; WO2014/129910; EP177640 WO2009/125292; WO2015/172787

The invention claimed is:
1. A method of processing lignocellulosic biomass by autohydrolysis, the method comprising the steps of:

providing lignocellulosic biomass feedstock wheat or other straw, subjecting the lignocellulosic biomass feedstock to mechanical compression using a mechanical or hydraulic piston compression system prior to hydrothermal pretreatment to produce a briquette, wherein the briquette has a diameter of greater than 25 mm, wherein a fiber structure of the lignocellulosic biomass feedstock wheat or other straw is substantially preserved, subjecting said lignocellulosic biomass feedstock wheat or other straw to hydrothermal pretreatment at a water content during pretreatment, of at least 40% for a residence time of between 1 and 120 minutes at a temperature between 160° and 220° C. wherein water is added as steam condensate in the case of pre-wetted feedstocks or for dry feed-stocks by homogeneous rapid absorption of water content added at reactor temperature and pressure, in batch-mode in an unagitated pressure reactor in such manner that agitation of the feedstock during pretreatment is avoided either by mechanical means or by explosive release of pretreated material to lower pressure, removing pretreated lignocellulosic biomass feedstock wheat or other straw from the pressure reactor, and sequentially repeating the batch-mode pretreatment so as to maintain a semi-continuous process, wherein a quantity of biomass is used to fill the pressure reactor in which the biomass is pretreated and then removed without additional loading and unloading of the reactor during the pretreatment of said quantity of biomass;

wherein the lignocellulosic biomass feedstock wheat or other straw has a rapid hydration swelling factor of at least 7.

2. The method of claim 1, further comprising performing anaerobic digestion of the hydrothermally pretreated biomass to biogas.

3. The method of claim 1, wherein initial particle size reduction prior to compression achieves pieces having lengths between 2-25 mm.

4. The method of claim 1, wherein the lignocellulosic biomass feedstock wheat or other straw has been subjected to mechanical compression at moisture content not more than 20% w/w.

5. The method of claim 1, wherein the lignocellulosic biomass feedstock wheat or other straw is compressed using piston compression or ring die where the applied pressure is less than 500 bar (atmospheric).

6. The method of claim 1, wherein the lignocellulosic biomass feedstock wheat or other straw is introduced into the reactor dry having water content <25% by weight after which water is added within the pressure reactor at a temperature between 100-220° C. sufficient to adjust dry matter (DM) content of the compressed biomass to between 15-50% by weight after which a temperature of between 160-220° C. is maintained for between 1 minute and 120 minutes.

7. The method of claim 1, wherein the lignocellulosic biomass feedstock wheat or other straw is pre-wetted prior to hydrothermal pretreatment.

8. The method of claim 1, wherein unagitated hydrothermal pretreatment is conducted with packing density in the occupied reactor volume between 0.08 and 0.35 kg DM/liter.

9. The method of claim 1, wherein hydrothermal pretreatment is conducted with average quantities of biomass in each batch of at least 5 kg DM content.

10. The method of claim 1, wherein reactor pressure at the end of pretreatment is vented to an over-pressure of not more than 4 bar after which this overpressure is used to purge pretreated biomass from the reactor.

11. The method of claim 1, wherein pretreated biomass is purged from the reactor by washing with water content, either without use of over-pressure or in combination with use of over-pressure.

12. A method of processing lignocellulosic biomass by autohydrolysis, the method comprising the steps of:

providing wheat or other straw, compressing the wheat or other straw with an applied pressure less than 500 bar (atmospheric) by piston compression briquetting in such a manner that the fiber structure of the wheat or other straw is substantially preserved, wherein the compressed wheat or other straw has a specific density at least 500 kg/m3, wherein the compressed wheat or other straw exhibits a time to swelling factor of less than 12.0 or a rapid hydration swelling factor of at least 7.0 or both, and wherein the compressed wheat or other straw is in a briquette having a diameter greater than 25 mm, and subjecting said compressed straw to continuous hydrothermal pretreatment in an unagitated pressure reactor for a residence time of between 1 and 120 minutes at a temperature between 160° and 220° C. in such manner that agitation of the feedstock during pretreatment is avoided either by mechanical means or by explosive release of pretreated material to lower pressure, wherein water content during pretreatment is at least 40%.

13. The method of claim 12 wherein water content during pretreatment is achieved primarily by adding water to the wheat or other straw inside the reactor when it is pressurized.

14. The method of claim 12 wherein the wheat or other straw is pre-wetted prior to hydrothermal pretreatment.

15. The method of claim 12, further comprising performing anaerobic digestion of the hydrothermally pretreated biomass to biogas.

16. A method of processing lignocellulosic biomass by autohydrolysis, the method comprising the steps of:

providing lignocellulosic biomass feedstock wherein the lignocellulosic biomass feedstock is wheat or other straw;

subjecting the lignocellulosic biomass feedstock to mechanical compression to produce a briquette having a diameter of greater than 25 mm, wherein a fiber structure of the lignocellulosic biomass feedstock is substantially preserved;

pretreating the lignocellulosic biomass feedstock by hydrothermal pretreatment at a water content during pretreatment of at least 40% for a residence time of between 1 and 120 minutes at a temperature between 160° and 220° C. wherein water is added as steam condensate in the case of pre-wetted feedstocks or for dry feed-stocks by homogeneous rapid absorption of water content added at reactor temperature and pressure, in batch-mode in an unagitated pressure reactor in such manner that agitation of the feedstock during pretreatment is avoided either by mechanical means or by explosive release of pretreated material to lower pressure, removing the pretreated lignocellulosic biomass feedstock from the pressure reactor; and sequentially repeating pretreatment so as to maintain a semi-continuous process, wherein a quantity of biomass is used to fill the pressure reactor in which the biomass is pretreated and then removed without additional loading and unloading of the reactor during the pretreatment of said quantity of biomass.

17. The method according to claim 16, wherein the lignocellulosic biomass feedstock has a time to swelling factor of less than 12.0, a rapid hydration swelling factor of at least 7.0, or both.

\* \* \* \* \*